United States Patent
Nagele

(10) Patent No.: US 12,174,187 B2
(45) Date of Patent: Dec. 24, 2024

(54) METHODS FOR DETECTING MULTIPLE SCLEROSIS (MS) DIAGNOSTIC AUTOANTIBODIES

(71) Applicant: Rowan University, Glassboro, NJ (US)

(72) Inventor: Robert G. Nagele, Turnersville, NJ (US)

(73) Assignee: Rowan University, Glassboro, NJ (US)

( * ) Notice: Subject to any disclaimer, the term of this patent is extended or adjusted under 35 U.S.C. 154(b) by 41 days.

(21) Appl. No.: 17/820,803

(22) Filed: Aug. 18, 2022

(65) Prior Publication Data

US 2022/0390447 A1   Dec. 8, 2022

Related U.S. Application Data

(63) Continuation of application No. 16/611,951, filed as application No. PCT/US2018/032130 on May 10, 2018, now abandoned.

(60) Provisional application No. 62/504,130, filed on May 10, 2017.

(51) Int. Cl.
| | | |
|---|---|---|
| *G01N 33/564* | (2006.01) | |
| *G01N 33/53* | (2006.01) | |
| *G01N 33/552* | (2006.01) | |

(52) U.S. Cl.
CPC .......... *G01N 33/564* (2013.01); *G01N 33/53* (2013.01); *G01N 33/552* (2013.01); *G01N 2800/285* (2013.01); *G01N 2800/50* (2013.01); *G01N 2800/56* (2013.01)

(58) Field of Classification Search
None
See application file for complete search history.

(56) References Cited

U.S. PATENT DOCUMENTS

| | | |
|---|---|---|
| 3,817,837 A | 6/1974 | Rubenstein |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 4,376,110 A | 3/1983 | David et al. |
| 5,143,854 A | 9/1992 | Pirrung et al. |
| 5,384,261 A | 1/1995 | Winkler et al. |
| 5,424,186 A | 6/1995 | Fodor et al. |
| 5,445,934 A | 8/1995 | Fodor et al. |
| 5,547,839 A | 8/1996 | Dower et al. |
| 5,578,832 A | 11/1996 | Trulson et al. |
| 5,631,734 A | 5/1997 | Stern et al. |
| 5,677,195 A | 10/1997 | Winkler et al. |
| 5,708,153 A | 1/1998 | Dower et al. |
| 5,744,305 A | 4/1998 | Fodor et al. |
| 5,770,358 A | 6/1998 | Dower et al. |
| 5,789,162 A | 8/1998 | Dower et al. |
| 5,800,992 A | 9/1998 | Fodor et al. |
| 5,834,758 A | 11/1998 | Trulson et al. |
| 5,837,832 A | 11/1998 | Chee et al. |
| 5,856,092 A | 1/1999 | Dale et al. |
| 5,856,174 A | 1/1999 | Lipshutz et al. |
| 5,861,242 A | 1/1999 | Chee et al. |
| 5,902,723 A | 5/1999 | Dower et al. |
| 5,922,591 A | 7/1999 | Anderson et al. |
| 5,936,324 A | 8/1999 | Montagu |
| 5,981,956 A | 11/1999 | Stern |
| 6,025,601 A | 2/2000 | Trulson et al. |
| 6,027,880 A | 2/2000 | Cronin et al. |
| 6,040,193 A | 3/2000 | Winkler et al. |
| 6,090,555 A | 7/2000 | Fiekowsky et al. |
| 6,141,096 A | 10/2000 | Stern et al. |

(Continued)

FOREIGN PATENT DOCUMENTS

| | | |
|---|---|---|
| WO | 99/47964 A1 | 9/1999 |
| WO | 2011142900 A1 | 11/2011 |

(Continued)

OTHER PUBLICATIONS

Reidhammer at al., Antigen presentation, autoantigens, and immune regulation in multiple sclerosis and other autoimmune diseases. Front. Immunol., Jun. 17, 2015, vol. 6, p. 322 (pp. 1-23).

Francisco J. Quintana et al., Antigen microarrays identify unique serum autoantibody signatures in clinical and pathologic subtypes of multiple sclerosis, Proceedings of the National Academy of Sciences, National Academy of Sciences, Vo. 105, No. 48, Feb. 12, 2008, pp. 18889-18894.

Veerle Somers, et al., Autoantibody profiling in multiple sclerosis reveals novel antigenic candidates, The Journal of Immunology, vol. 180, No. 6, Mar. 5, 2008, pp. 3957-3963.

Somers, K. et al., Multiplexing approaches for autoantibody profiling in multiple sclerosis, Autoimmunity Reviews, Elsevier, Amsterdam, NL, vol. 8, No. 7, Jun. 1, 2009, pp. 573-579.

(Continued)

*Primary Examiner* — Amy E Juedes
*Assistant Examiner* — Peter Johansen
(74) *Attorney, Agent, or Firm* — Fox Rothschild LLP

(57) ABSTRACT

Methods for detecting Multiple Sclerosis (MS) diagnostic autoantibodies in a subject and generating a subject-specific, MS diagnostic autoantibody profile are described. The methods include contacting an immunoglobulin-containing biological sample from the subject with a system comprising antigens that form immunocomplexes with MS diagnostic autoantibodies, the antigens including general transcription factor II-I, splicing factor 1, and inducible T-cell co-stimulator (ICOS), to form a reaction mixture, under conditions that allow for formation in the reaction mixture of an immunocomplex between each antigen and its corresponding MS diagnostic autoantibody, if its corresponding MS diagnostic autoantibody is present in the sample; and detecting presence or absence of immunocomplexes in the reaction mixture, wherein formation of immunocomplexes between the antigens and their corresponding MS diagnostic autoantibodies indicates presence of the MS diagnostic autoantibodies in the biological sample.

20 Claims, 4 Drawing Sheets

(56) References Cited

U.S. PATENT DOCUMENTS

| | | |
|---|---|---|
| 6,185,030 B1 | 2/2001 | Overbeck |
| 6,201,639 B1 | 3/2001 | Overbeck |
| 6,218,803 B1 | 4/2001 | Montagu et al. |
| 6,225,625 B1 | 5/2001 | Pirrung et al. |
| 7,144,699 B2 | 12/2006 | Chee |
| 7,300,788 B2 | 11/2007 | Matsuzaki et al. |
| 7,317,415 B2 | 1/2008 | Kaiser |
| 7,413,862 B2 | 8/2008 | van Dongen et al. |
| 7,689,022 B2 | 3/2010 | Weiner et al. |
| 2005/0032074 A1 | 2/2005 | Shah et al. |
| 2013/0157888 A1 | 6/2013 | Nagele |

FOREIGN PATENT DOCUMENTS

| | | |
|---|---|---|
| WO | 2013010003 A1 | 1/2013 |
| WO | 2013023144 A2 | 2/2013 |

OTHER PUBLICATIONS

Belogurov, Alexey A. et al., Recognition and degradation of myelin bosic protein peptides by serum autoantibodies: 5 novel biomarker for multiple sclerosis, The Journal of Immonology, American Association of Immunologists, US, vol. 18, No. 2, Jan. 15, 2008, pp. 1258-167.

FIG. 3

| Group | n | Age (Years) | (Range) | Sex (% Female) | Ethnicity (% Caucasian) |
|---|---|---|---|---|---|
| Multiple Sclerosis | 51 | 48.8 ± 10.7 | 25-67 | 75 | 96 |
| -Relapsing-Remitting | 31 | 45.8 ± 11.1 | 25-67 | 81 | 94 |
| -Secondary Progressive | 20 | 53.5 ± 8.0 | 36-67 | 65 | 100 |
| Controls | 31 | 53.7 ± 13.4 | 30-79 | 81 | 100 |
| Early-Stage Parkinson's Disease | 15 | 63.5 ± 6.8 | 51-73 | 80 | 100 |
| Breast Cancer | 15 | 52.3 ± 6.6 | 45-63 | 100 | 87 |

FIG. 4

| MS (n=25) vs. | 50 Markers | | | 3 Markers | | |
|---|---|---|---|---|---|---|
| | Age Matched Controls | Early-Stage PD | Breast Cancer | Age Matched Controls | Early-Stage PD | Breast Cancer |
| n | 15 | 15 | 15 | 15 | 15 | 15 |
| Sensitivity | 100.0 | 48.0 | 100.0 | 100.0 | 76.0 | 100.0 |
| Specificity | 86.7 | 26.7 | 100.0 | 86.7 | 6.7 | 100.0 |
| PPV | 92.6 | 52.2 | 100.0 | 92.6 | 57.6 | 100.0 |
| NPV | 100.0 | 23.5 | 100.0 | 100.0 | 14.3 | 100.0 |
| Overall Accuracy % | 95.0 | 40.0 | 100.0 | 95.0 | 50.0 | 100.0 |
| Overall Error % | 5.0 | 60.0 | 0.0 | 5.0 | 50.0 | 0.0 |

FIG. 5

| MS (n=25) vs. | 50 Markers | | | 3 Markers | | |
|---|---|---|---|---|---|---|
| | AUC (95% CI) | Sensitivity (95% CI) | Specificity (95% CI) | AUC (95% CI) | Sensitivity (95% CI) | Specificity (95% CI) |
| Age Matched Controls (n=15) | 0.94 (0.82, 1) | 1 (1, 1) | 0.93 (0.80, 1) | 0.96 (0.87, 1) | 0.96 (0.88, 1) | 0.93 (0.80, 1) |
| Early-Stage PD (n=15) | 0.72 (0.56, 0.88) | 0.80 (0.64, 0.96) | 0.60 (0.33, 0.87) | 0.61 (0.44, 0.78) | 0.48 (0.32, 0.68) | 0.87 (0.67, 1) |
| Breast Cancer (n=15) | 1 | 1 | 1 | 1 | 1 | 1 |

METHODS FOR DETECTING MULTIPLE SCLEROSIS (MS) DIAGNOSTIC AUTOANTIBODIES

CROSS-REFERENCE TO RELATED APPLICATIONS

This application is a continuation of U.S. patent application Ser. No. 16/611,951, filed Nov. 8, 2019, which is a 35 U.S.C. § 371 national phase application of International Application No. PCT/US2018/032130, filed May 10, 2018, which claims priority under 35 U.S.C. § 119(e) to U.S. Provisional Application No. 62/504,130, filed May 10, 2017, all of which are incorporated herein by reference in their entireties.

BACKGROUND OF THE INVENTION

Multiple Sclerosis (MS) is a neuroinflammatory autoimmune disease that primarily affects white matter of the central nervous system (CNS). Recent estimates show between 250,000 and 350,000 people in the United States currently suffer from MS. As is the case with many autoimmune conditions, women are disproportionately affected by MS, with a ratio of three women for every one man diagnosed. The reason for this discrepancy in gender is unknown, but it is speculated to be influenced by hormonal, genetic, or environmental differences. MS is traditionally pathologically characterized by subcortical white matter lesions separated temporally and spatially, with microscopic structural defects accruing in the myelin sheaths that insulate axons for proper neuronal firing. Demyelination occurs commonly in the white matter of the brain, including in the optic nerve and spinal cord, but later progresses to include gray matter lesions that are readily visualized in magnetic resonance images (MRIs). Common symptoms include lower extremity muscle weakness, paresthesia, and vision changes, and cognitive decline is later observed as the disease progresses.

Presently, a diagnosis of MS requires a thorough patient history, imaging such as MRI to detect white matter lesions, an electrophysiological examination using evoked potential tests, and/or cerebrospinal fluid (CSF) analysis to detect the presence of increased immunoglobulin species. While some success has been achieved to accurately diagnose and treat the symptoms of certain patients, others succumb to progressively worsening disease symptoms and opportunistic conditions.

There is thus a need in the art for methods and compositions for detecting, subtyping, and/or assessing progression of MS in a subject. Such methods and compositions should allow for rapid evaluation of a subject who may have or not detectable physical symptoms of MS. The present invention meets these needs.

BRIEF SUMMARY OF THE INVENTION

The present invention provides a method for detecting Multiple Sclerosis (MS) diagnostic autoantibodies in a subject. The present invention further provides a method of generating a subject-specific, MS-specific autoantibody profile for a subject. The invention further provides a kit for detecting MS diagnostic biomarkers. The present invention further provides a method of subtyping MS in a subject. The present invention further provides a method of identifying the pathological progression of MS in a subject in need thereof. The present invention further comprises a method of identifying a subject at risk of suffering from RRMS. The present invention further comprises a method of identifying a subject at risk of suffering from SPMS.

In certain embodiments, the method comprises contacting an immunoglobulin-containing biological sample from the subject with a system comprising one or more autoantigens to form a reaction mixture, under conditions that allow for formation in the reaction mixture of an immunocomplex between each autoantigen and its corresponding autoantibody, if its corresponding autoantibody is present in the sample. In other embodiments, the one or more autoantigens comprise BC099907.1, NM_201998.1, and BC028006.1. In yet other embodiments, the method comprises detecting presence or absence of immunocomplexes in the reaction mixture, wherein formation of an immunocomplex between an autoantibody and its corresponding autoantigen indicates presence of the autoantibody in the biological sample. In yet other embodiments, the method comprises generating a subject-specific MS-specific autoantibody profile of autoantibodies present in the biological sample.

In certain embodiments, the one or more autoantigens further comprise at least one selected from the group consisting of NM_020317.2, NM_001008737.1, NM_004912.3, BC001419.1, NM_002642.1, PV4202, and NM_016011.2.

In certain embodiments, the one or more autoantigens further comprise at least one selected from the group consisting of BC001419.1 and NM_016011.2.

In certain embodiments, the subject is a human.

In certain embodiments, the biological sample is selected from the group consisting of whole blood, plasma, serum, cerebrospinal fluid, saliva, and sputum. In other embodiments, the biological sample is whole blood.

In certain embodiments, at least one autoantigen is attached to a solid substrate. In other embodiments, each one of the autoantigens is attached to a solid substrate and is in the form of an array. In yet other embodiments, the array is a microarray. In yet other embodiments, the solid substrate is a nitrocellulose-coated glass slide.

In certain embodiments, the immunocomplex is detected using an immunoassay. In other embodiments, the immunoassay comprises a competition assay, direct immunoassay, indirect immunoassay, immunoprecipitation, immunoblotting, and/or sandwich immunoassay.

In certain embodiments, the subject is advised to be administered a therapeutic agent and/or receive therapeutic intervention for MS. In other embodiments, the method further comprises administering to the subject a therapeutic agent and/or a therapeutic intervention to treat MS.

In certain embodiments, the method comprises contacting an immunoglobulin-containing biological sample from the subject with a system comprising one or more relapsing-remitting MS (RRMS)-specific autoantigens and/or one or more secondary progressive (SPMS)-specific autoantigens to form a reaction mixture, under conditions that allow for formation in the reaction mixture of an immunocomplex between each autoantigen and its corresponding autoantibody, if its corresponding autoantibody is present in the sample. In other embodiments, the one or more RRMS-specific autoantigens comprise at least one selected from the group consisting of NM_152729.2, BC024289.1, BC020233.1, BC030813.1, NM_144606.1, and NM_145253.1. In yet other embodiments, the one or more SPMS-specific autoantigens comprise at least one selected from the group consisting of NP_002497.2, NP_001001547.1, NM_004493.1, NM_018464.2, BC010467.1, NM_005409.3, BC048299.1, NM_022788.2, NP_000556.1, and BC093661.1. In yet other embodiments, the method comprises detecting presence or absence of immunocomplexes in the reaction mixture, wherein formation of an immunocomplex between an autoantibody and its corresponding autoantigen indicates presence of the autoantibody in the sample. In yet other embodiments, presence of at least one RRMS-specific immunocomplex in the reaction mixture indicates a RRMS subtype. In yet other embodiments, presence of at least one SPMS-specific immunocomplex in the reaction mixture indicates a SPMS subtype. In yet other embodiments, presence of at least one RRMS-specific immunocomplex in the reaction mixture indicates the subject has risk of suffering from or developing RRMS. In yet other embodiments, presence of at least one SPMS-specific immunocomplex in the reaction mixture indicates that the subject has risk of suffering from or developing SPMS.

In certain embodiments, the one or more RRMS-specific autoantigens comprise at least one selected from the group consisting of NM_152729.2, BC024289.1, and BC020233.1.

In certain embodiments, the one or more RRMS-specific autoantigens further comprise at least one selected from the group consisting of NM_005151.2, NM_004987.3, NM_003141.2, and NP_002167.1.

In certain embodiments, the one or more SPMS-specific autoantigens comprise at least one selected from the group consisting of NP_002497.2, NP_001001547.1, NM_004493.1, NM_018464.2, and NP_000556.1.

In certain embodiments, the subject is a human. In other embodiments, the biological sample is selected from the group consisting of whole blood, plasma, serum, cerebrospinal fluid, saliva, and sputum. In yet other embodiments, the biological sample is whole blood.

In certain embodiments, at least one autoantigen is attached to a solid substrate. In other embodiments, each one of the autoantigens is attached to a substrate and is in the form of an array. In yet other embodiments, the array is a microarray. In yet other embodiments, the substrate is a nitrocellulose-coated glass slide.

In certain embodiments, the immunocomplex is detected using an immunoassay. In other embodiments, the immunoassay comprises a competition assay, direct immunoassay, indirect immunoassay, immunoprecipitation, immunoblotting, and/or sandwich immunoassay.

In certain embodiments, the subject is advised to be administered a therapeutic agent and/or receive therapeutic intervention for MS. In other embodiments, the method further comprises administering to the subject a therapeutic agent and/or a therapeutic intervention to treat MS.

In certain embodiments, the kit comprises an array comprising a solid substrate and one or more autoantigens immobilized onto the substrate, wherein the one or more autoantigens in the array comprise at least one selected from the first autoantigen group consisting of: BC099907.1, NM_201998.1, BC028006.1, NM_020317.2, NM_003636.1, BC003065.1, NM_001008737.1, XM_003960444.1, BC029796.1, NM_152716.1, XM_379114.1, BC022258.1, BC002733.2, NM_004912.3, BC001419.1, NM_002642.1, PV4202, PV4337, XM_378514.1, XM_086879.4, BC015514.1, NM_005151.2, BC016380.1, BC032451.1, NM_175907.3, BC073782.1, NM_004987.3, BC022362.1, NM_004302, NM_003141.2, NM_005522.3, NM_016011.2, NM_005734.1, NM_004329, NP_002167.1, BC014991.1, NM_004527.2, BC014271.2, XM_378660.1, NM_020467.2, BC033792.1, NM_007255.1, BC017054.1, NM_180699.1, NM_172159.2, NM_199183.1, BC002448.2, NM_005435.2, BC006105.1, and NM_005371.2. In other embodiments, the one or more autoantigens in the array comprise BC099907.1, NM_201998.1, and BC028006.1. In yet other embodiments, the one or more autoantigens in the array further comprise at least one selected from the group consisting of NM_020317.2, NM_001008737.1, NM_004912.3, BC001419.1, NM_002642.1, PV4202, and NM_016011.2. In yet other embodiments, the one or more autoantigens in the array further comprise at least one selected from the group consisting of BC001419.1 and NM_016011.2. In yet other embodiments, the only autoantigens in the array are the at least one selected from the first autoantigen group. In yet other embodiments, the only autoantigens in the array are BC099907.1, NM_201998.1, and BC028006.1. In yet other embodiments, the only autoantigens in the array are BC099907.1, NM_201998.1, BC028006.1, and at least one selected from the group consisting of NM_020317.2, NM_001008737.1, NM_004912.3, BC001419.1, NM_002642.1, PV4202, and NM_016011.2. In yet other embodiments, the only autoantigens in the array are BC099907.1, NM_201998.1, BC028006.1, and at least one selected from the group consisting of BC001419.1 and NM_016011.2.

In certain embodiments, the kit comprises an array comprising a solid substrate and one or more autoantigens immobilized onto the substrate, wherein the one or more autoantigens in the array comprise at least one selected from the following groups: a RRMS-specific autoantigen group comprising at least one selected from the group consisting of NM_152729.2, BC024289.1, BC020233.1, BC030813.1, NM_144606.1, and NM_145253.1, and a SPMS-specific autoantigen group comprising at least one selected from the group consisting of NP_002497.2, NP_001001547.1, NM_004493.1, NM_018464.2, BC010467.1, NM_005409.3, BC048299.1, NM_022788.2, NP_000556.1, and BC093661.1. In other embodiments, the RRMS-specific autoantigen comprises at least one selected from the group consisting of NM_152729.2, BC024289.1, and BC020233.1. In yet other embodiments, the one or more RRMS-specific autoantigens further comprise at least one selected from the group consisting of NM_005151.2, NM_004987.3, NM_003141.2, and NP_002167.1. In yet other embodiments, the one or more SPMS-specific autoantigens comprise at least one selected from the group consisting of NP_002497.2, NP_001001547.1, NM_004493.1, NM_018464.2, and NP_000556.1. In yet other embodiments, the only autoantigens in the array are the at least one selected from the RRMS-specific autoantigen group and the SPMS-specific autoantigen group.

In certain embodiments, the only autoantigen in the array is at least one selected from the group consisting of NM_152729.2, BC024289.1, BC020233.1, BC030813.1, NM_144606.1, and NM_145253.1. In other embodiments, the only autoantigen in the array is at least one selected from the group consisting of NM_152729.2, BC024289.1, and BC020233.1. In yet other embodiments, the only autoantigen in the array is at least one selected from the group consisting of NM_005151.2, NM_004987.3, NM_003141.2, and NP_002167.1. In yet other embodiments, the only autoantigen in the array is at least one selected from the group consisting of NP_002497.2, NP_001001547.1, NM_004493.1, NM_018464.2, BC010467.1, NM_005409.3, BC048299.1, NM_022788.2, NP_000556.1, and BC093661.1. In yet other embodiments, the only autoantigen in the array is at least one selected from the group consisting of NP_002497.2, NP_001001547.1, NM_004493.1, NM_018464.2, and NP_000556.1. In yet other embodiments, the only autoantigens in the array are one of the following or any combinations thereof: (a) at least one selected from the group consisting of NM_152729.2, BC024289.1, BC020233.1, BC030813.1, NM_144606.1, and NM_145253.1; (b) at least one selected from the group consisting of NM_152729.2, BC024289.1, and BC020233.1; (c) at least one selected from the group consisting of NM_005151.2, NM_004987.3, NM_003141.2, and NP_002167.1; (d) at least one selected from the group consisting of NP_002497.2, NP_001001547.1, NM_004493.1, NM_018464.2, BC010467.1, NM_005409.3, BC048299.1, NM_022788.2, NP_000556.1, and BC093661.1; and (e) at least one selected from the group consisting of NP_002497.2, NP_001001547.1, NM_004493.1, NM_018464.2, and NP_000556.1.

In certain embodiments, the kit comprises assay reagents for detection of immunocomplexes formed by binding of the immobilized autoantigens contemplated in the invention to the MS diagnostic autoantibody biomarkers in an immunoglobulin-containing biological sample from a subject.

In certain embodiments, the kit comprises a package labeling indicating a diagnosis of MS in the subject upon detecting formation of at least one immunocomplex from the first autoantigen group. In other embodiments, the kit comprises a package labeling indicating a diagnosis of RRMS in the subject upon detecting formation of at least one immunocomplex from the RRMS-specific autoantigen group. In yet other embodiments, the kit a package labeling indicating a diagnosis of SPMS in the subject upon detecting formation of at least one immunocomplex from the SPMS-specific autoantigen group.

In certain embodiments, the package labeling indicates that the subject has about 90% risk of developing MS within the next 1 to 10 years when immunocomplexes are detected for all three of BC099907.1, NM_201998.1, and BC028006.1.

In certain embodiments, the array is an ordered microarray. In other embodiments, the substrate is a nitrocellulose-coated glass slide.

BRIEF DESCRIPTION OF THE DRAWINGS

The following detailed description of specific embodiments of the invention will be better understood when read in conjunction with the appended drawings. For the purpose of illustrating the invention, exemplary embodiments are shown in the drawings. It should be understood, however, that the invention is not limited to the precise arrangements and instrumentalities of the embodiments shown in the drawings.

FIG. 3 is a table illustrating sample demographics. The number of individuals (n), age, range of age, gender, and ethnicity are listed for each disease and control group.

FIG. 4 is a table illustrating diagnostic results using a panel of 50 and a panel of 3 mixed-MS biomarkers and RF. Diagnostic performance was assessed using RF. Using Testing Set samples, RF successfully distinguished MS subjects (n=25) from age-matched and gender-matched controls as well as those with breast cancer with high overall accuracies. RF was unable to accurately distinguish MS subjects from those with early-stage PD using the selected biomarkers.

FIG. 5 is a table illustrating ROC curve assessment of diagnostic utility of the top 50 and top 3 depleted mixed MS biomarkers. ROC curve analyses (Testing Set subjects only) show the diagnostic utility of the top 50 and top 3 depleted biomarkers for distinguishing MS subjects from age-matched controls and from early-stage PD and breast cancer. Area under the curve (AUC) values at 95% confidence are listed along with values for sensitivity and specificity derived from ROC curve output data.

DETAILED DESCRIPTION OF THE INVENTION

Figure 1:
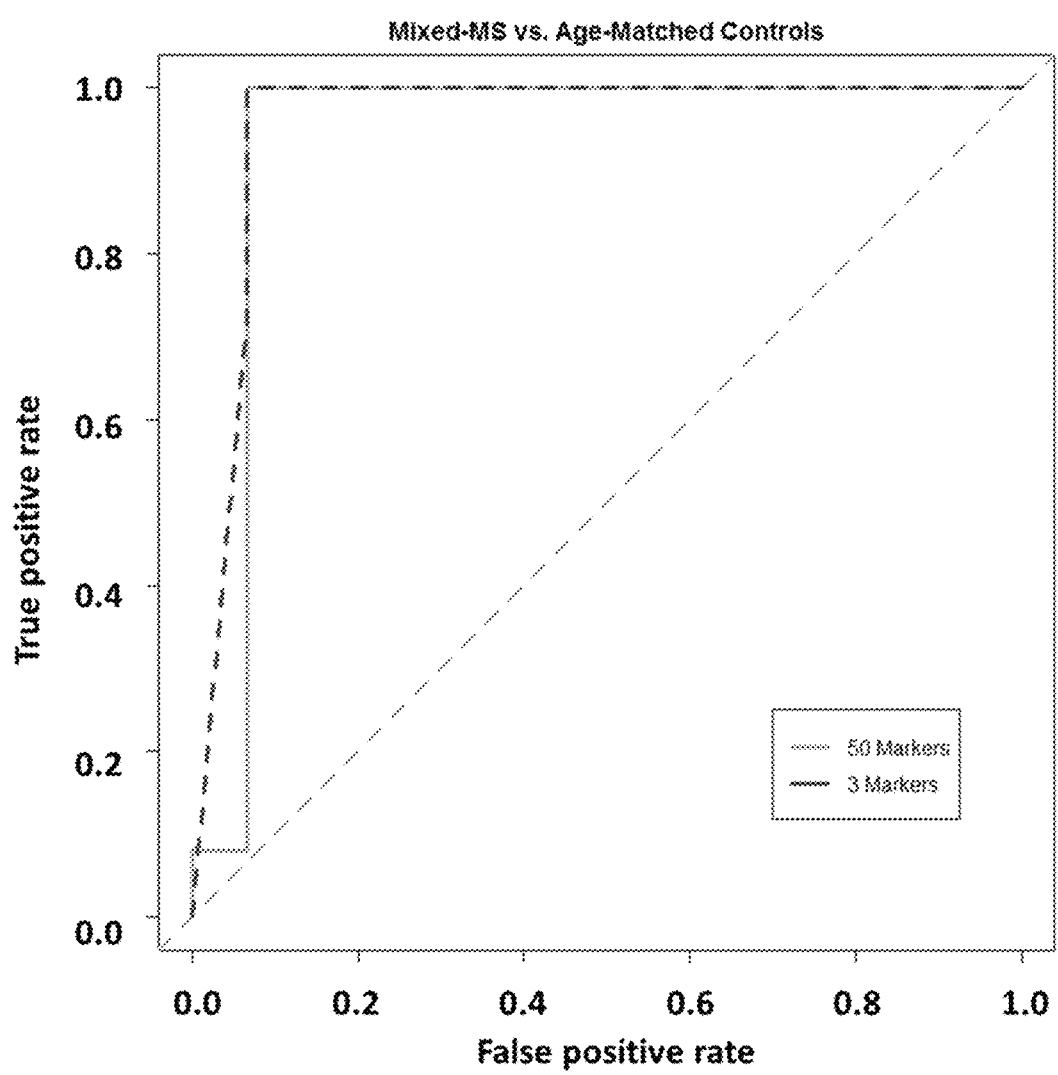
FIG. 1 is a graph illustrating biomarker analysis and Receiver Operating Characteristic (ROC) curve assessment of diagnostic utility of autoantibody biomarkers for the detection of MS. ROC assessment of autoantibody biomarkers was performed as to detection of mixed-MS in Testing Set subjects. Comparison of MS (n=25) vs. age- and gender-matched controls (n=15) using a panel of 50 (solid line) or a panel of 3 (dashed line) MS-specific biomarkers demonstrates that these biomarker panels can be used to detect MS with high overall accuracy. The diagonal dashed line represents the line of no discrimination. The ROC AUC, sensitivity, and specificity values for the panels of 50 and 3 biomarkers are shown in the Table found in FIG. 5.

In one aspect, the present invention relates to the identification of autoantibody biomarkers that are useful for the detection and/or progression evaluation of Multiple Sclerosis (MS).

In one aspect, the present invention provides a method for detecting certain MS-related autoantibody biomarkers in a subject in need of such detection. In certain embodiments, the method comprises obtaining an immunoglobulin-containing biological sample from the subject. In other embodiments, the method comprises determining in the biological sample presence or absence of an autoantibody that binds to a specific autoantigen to form corresponding an immunocomplex, wherein formation of the immunocomplex between the autoantibody and the autoantigen indicates presence of the autoantibody in the sample. In yet other embodiments, presence or absence of the immunocomplex in the biological sample can be used to identify the presence of ongoing MS pathology in the subject, and/or identify the subject as having early-stage MS and at risk for developing MS symptoms, and/or identify the specific clinical progression of MS in the subject.

In another aspect, the present invention provides a method for detecting MS diagnostic autoantibodies in a subject in need thereof. In certain embodiments, the method comprises obtaining an immunoglobulin-containing biological sample from the subject. In other embodiments, the method comprises contacting the biological sample with a system comprising one or more autoantigens to form a reaction mixture, under conditions that allow for formation in the reaction mixture of an immunocomplex between each autoantigen and its corresponding autoantibody, if its corresponding autoantibody is present in the sample. In yet other embodiments, the one or more autoantigens comprise BC099907.1, NM_201998.1, and BC028006.1. In yet other embodiments, the one or more autoantigens further comprise at least one, two, three, four, five, six, or seven selected from the group consisting of NM_020317.2, NM_001008737.1, NM_004912.3, BC001419.1, NM_002642.1, PV4202, and NM_016011.2. In yet other embodiments, the one or more autoantigens further comprise at least one or two selected from the group consisting of BC001419.1 and NM_016011.2. In yet other embodiments, the method comprises detecting presence or absence of immunocomplexes in the reaction mixture, wherein formation of an immunocomplex between an autoantibody and the corresponding autoantigen indicates presence of the autoantibody in the sample.

In yet another aspect, the present invention provides a method of generating a subject-specific, MS-specific autoantibody profile. In certain embodiments, the method comprises obtaining an immunoglobulin-containing biological sample from the subject. In other embodiments, the method comprises contacting the biological sample with a system comprising one or more autoantigens to form a reaction mixture, under conditions that allow for formation in the reaction mixture of an immunocomplex between each autoantigen and its corresponding autoantibody, if its corresponding autoantibody is present in the sample. In yet other embodiments, the one or more autoantigens comprise BC099907.1, NM_201998.1, and BC028006.1. In yet other embodiments, the one or more autoantigens further comprise at least one, two, three, four, five, six, or seven selected from the group consisting of NM_020317.2, NM_001008737.1, NM_004912.3, BC001419.1, NM_002642.1, PV4202, and NM_016011.2.

In yet other embodiments, the one or more autoantigens further comprise at least one or two selected from the group consisting of BC001419.1 and NM_016011.2. In yet other embodiments, the method comprises detecting presence or absence of immunocomplexes in the reaction mixture, wherein formation of an immunocomplex between an autoantibody and the corresponding autoantigen indicates presence of the autoantibody in the sample. In yet other embodiments, the method comprises generating a subject-specific MS-specific autoantibody profile of autoantibodies present in the sample.

In yet another aspect, the present invention provides a method of subtyping MS in a subject in need thereof. In certain embodiments, the method comprises obtaining an immunoglobulin-containing biological sample from the subject. In other embodiments, the method comprises contacting the biological sample with a system comprising one or more relapsing-remitting MS (RRMS)-specific autoantigens and/or one or more secondary progressive (SPMS)-specific autoantigens to form a reaction mixture, under conditions that allow for formation in the reaction mixture of an immunocomplex between each autoantigen and its corresponding autoantibody, if its corresponding autoantibody is present in the sample. In yet other embodiments, the one or more RRMS-specific autoantigens comprise at least one, two, three, four, five, or six selected from the group consisting of NM_152729.2, BC024289.1, BC020233.1, BC030813.1, NM_144606.1, and NM_145253.1. In yet other embodiments, the one or more RRMS-specific autoantigens comprise at least one, two, or three selected from the group consisting of NM_152729.2, BC024289.1, and BC020233.1. In yet other embodiments, the one or more RRMS-specific antigens further comprise at least one, two, three, or four selected from the group consisting of NM_005151.2, NM_004987.3, NM_003141.2, and NP_002167.1. In yet other embodiments, the one or more SPMS-specific autoantigens comprise at least one, two, three, four, five, six, seven, eight, nine, or ten selected from the group consisting of NP_002497.2, NP_001001547.1, NM_004493.1, NM_018464.2, BC010467.1, NM_005409.3, BC048299.1, NM_022788.2, NP_000556.1, and BC093661.1. In yet other embodiments, the one or more SPMS-specific autoantigens comprise at least one, two, three, four, or five selected from the group consisting of NP_002497.2, NP_001001547.1, NM_004493.1, NM_018464.2, and NP_000556.1. In yet other embodiments, the method comprises detecting presence or absence of immunocomplexes in the reaction mixture, wherein formation of an immunocomplex between an autoantibody and the corresponding autoantigen indicates presence of the autoantibody in the sample. In yet other embodiments, presence of at least one RRMS-specific immunocomplex in the reaction mixture indicates a RRMS subtype. In yet other embodiments, presence of at least one SPMS-specific immunocomplex in the reaction mixture indicates a SPMS subtype.

In yet another aspect, the present invention provides a method of identifying the pathological progression of MS from one subtype to another in a subject in need thereof. In certain embodiments, the method comprises obtaining an immunoglobulin-containing biological sample from the subject. In other embodiments, the method comprises contacting the biological sample with a system comprising one or more relapsing-remitting MS (RRMS)-specific autoantigens and/or one or more secondary progressive (SPMS)-specific autoantigens to form a reaction mixture, under conditions that allow for formation in the reaction mixture of an immunocomplex between each autoantigen and its corresponding autoantibody, if its corresponding autoantibody is present in the sample. In yet other embodiments, the one or more RRMS-specific autoantigens comprise at least one, two, three, four, five, or six selected from the group consisting of NM_152729.2, BC024289.1, BC020233.1, BC030813.1, NM_144606.1, and NM_145253.1. In yet other embodiments, the one or more RRMS-specific autoantigens comprise at least one, two, or three selected from the group consisting of NM_152729.2, BC024289.1, and BC020233.1. In yet other embodiments, the one or more RRMS-specific antigens further comprise at least one, two, three, or four selected from the group consisting of NM_005151.2, NM_004987.3, NM_003141.2, and NP_002167.1. In yet other embodiments, the one or more SPMS-specific autoantigens comprise at least one, two, three, four, five, six, seven, eight, nine, or ten of NP_002497.2, NP_001001547.1, NM_004493.1, NM_018464.2, BC010467.1, NM_005409.3, BC048299.1, NM_022788.2, NP_000556.1, and BC093661.1. In yet other embodiments, the one or more SPMS-specific autoantigens comprise at least one, two, three, four, or five selected from the group consisting of NP_002497.2, NP_001001547.1, NM_004493.1, NM_018464.2, and NP_000556.1. In yet other embodiments, the method comprises detecting presence or absence of immunocomplexes in the reaction mixture, wherein formation of an immunocomplex between an autoantibody and the corresponding autoantigen indicates presence of the autoantibody in the sample. In yet other embodiments, presence of at least one RRMS-specific immunocomplex in the reaction mixture indicates a RRMS subtype. In yet other embodiments, presence of at least one SPMS-specific immunocomplex in the reaction mixture indicates a SPMS subtype.

In yet another aspect, the present invention provides a method of identifying a subject at risk of suffering from RRMS. In certain embodiments, the method comprises obtaining an immunoglobulin-containing biological sample from the subject. In other embodiments, the method comprises contacting the biological sample with a system comprising one or more relapsing-remitting MS (RRMS)-specific autoantigens, under conditions that allow for formation in the reaction mixture of an immunocomplex between each autoantigen and its corresponding autoantibody, if its corresponding autoantibody is present in the sample. In yet other embodiments, the one or more RRMS-specific autoantigens comprise at least one, two, three, four, five, or six selected from the group consisting of NM_152729.2, BC024289.1, BC020233.1, BC030813.1, NM_144606.1, and NM_145253.1. In yet other embodiments, the one or more RRMS-specific autoantigens comprise at least one, two, or three selected from the group consisting of NM_152729.2, BC024289.1, and BC020233.1. In yet other embodiments, the one or more RRMS-specific antigens further comprise at least one, two, three, or four selected from the group consisting of NM_005151.2, NM_004987.3, NM_003141.2, and NP_002167.1. In yet other embodiments, the method comprises detecting presence or absence of immunocomplexes in the reaction mixture, wherein formation of an immunocomplex between an autoantibody and the corresponding autoantigen indicates presence of the autoantibody in the sample. In yet other embodiments, presence of at least one RRMS-specific immunocomplex in the mixture indicate that the subject has risk of suffering from or developing RRMS.

In yet another aspect, the present invention provides a method of identifying a subject at risk of suffering from SPMS. In certain embodiments, the method comprises obtaining an immunoglobulin-containing biological sample from the subject. In other embodiments, the method comprises contacting the biological sample with a system comprising one or more secondary progressive (SPMS)-specific autoantigens to form a reaction mixture, under conditions that allow for formation in the reaction mixture of an immunocomplex between each autoantigen and its corresponding autoantibody, if its corresponding autoantibody is present in the sample. In yet other embodiments, the one or more SPMS-specific autoantigens comprise at least one, two, three, four, five, six, seven, eight, nine, or ten selected from the group consisting of NP_002497.2, NP_001001547.1, NM_004493.1, NM_018464.2, BC010467.1, NM_005409.3, BC048299.1, NM_022788.2, NP_000556.1, and BC093661.1. In yet other embodiments, the one or more SPMS-specific autoantigens comprise at least one, two, three, four, or five selected from the group consisting of NP_002497.2, NP_001001547.1, NM_004493.1, NM_018464.2, and NP_000556.1. In yet other embodiments, the method comprises detecting presence or absence of immunocomplexes in the reaction mixture, wherein formation of an immunocomplex between an autoantibody and its corresponding autoantigen indicates presence of the autoantibody in the sample. In yet other embodiments, presence of at least one SPMS-specific immunocomplex in the reaction mixture indicates that the subject has risk of suffering from or developing SPMS.

In yet another aspect, the present invention provides a kit for detecting MS diagnostic biomarkers. In certain embodiments, the kit comprises at least 1-50 autoantigen(s) selected from the group consisting of BC099907.1, NM_201998.1, BC028006.1, NM_020317.2, NM_003636.1, BC003065.1, NM_001008737.1, XM_003960444.1, BC029796.1, NM_152716.1, XM_379114.1, BC022258.1, BC002733.2, NM_004912.3, BC001419.1, NM_002642.1, PV4202, PV4337, XM_378514.1, XM_086879.4, BC015514.1, NM_005151.2, BC016380.1, BC032451.1, NM_175907.3, BC073782.1, NM_004987.3, BC022362.1, NM_004302, NM_003141.2, NM_005522.3, NM_016011.2, NM_005734.1, NM_004329, NP_002167.1, BC014991.1, NM_004527.2, BC014271.2, XM_378660.1, NM_020467.2, BC033792.1, NM_007255.1, BC017054.1, NM_180699.1, NM_172159.2, NM_199183.1, BC002448.2, NM_005435.2, BC006105.1, and NM_005371.2. In yet other embodiments, the kit comprises at least one, two, or three autoantigen selected from the group consisting of BC099907.1, NM_201998.1, and BC028006.1. In yet other embodiments, the kit comprises each one, two, or three from the group consisting of BC099907.1, NM_201998.1, and BC028006.1. In yet other embodiments, the kit further comprises at least one, two, three, four, five, six, or seven selected from the group consisting of NM_020317.2, NM_001008737.1, NM_004912.3, BC001419.1, NM_002642.1, PV4202, and NM_016011.2. In other embodiments, the kit comprises assay reagents for detecting at least one immunocomplex formed by the binding of at least one autoantigen of the kit with a MS diagnostic autoantibody in an immunoglobulin-containing biological sample from a subject. In yet other embodiments, the kit comprises a package labeling indicating a diagnosis of MS in a subject upon detecting formation of at least one immunocomplex between at least one antigen of the kit, with MS diagnostic autoantibody biomarkers obtained from the immunoglobulin-containing biological sample. In yet other embodiments, the subject has an about 90% risk of developing MS within the next 1 to 10 years when immunocomplex formation is detected for each one of BC099907.1, NM_201998.1, and BC028006.1. In yet other embodiments, the at least one antigen is immobilized on a substrate. In yet other embodiments, the subject has a diagnosis of MS when immunocomplex formation is detected for each one of BC099907.1, NM_201998.1, BC028006.1, and for at least one, two, three, four, five, six, or seven selected from the group consisting of NM_020317.2, NM_001008737.1, NM_004912.3, BC001419.1, NM_002642.1, PV4202, and NM_016011.2.

In certain embodiments, the subject is a human. In other embodiments, the biological sample is selected from the group consisting of whole blood, plasma, serum, cerebrospinal fluid, saliva, and sputum. In yet other embodiments, the biological sample is whole blood. The antigens can be attached to a substrate, preferably a nitrocellulose-coated glass slide, and can be in the form of an array, preferably a microarray.

DETAILED DESCRIPTION OF THE INVENTION

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, and immunology are those well-known and commonly employed in the art.

As used herein, the articles "a" and "an" refer to one or to more than one (i.e. to at least one) of the grammatical object of the article. By way of example, "an element" means one element or more than one element.

The term "abnormal" when used in the context of organisms, tissues, cells or components thereof, refers to those organisms, tissues, cells or components thereof that differ in at least one observable or detectable characteristic (e.g., age, treatment, time of day, and so forth) from those organisms, tissues, cells or components thereof that display the "normal" (expected) respective characteristic. Characteristics that are normal or expected for one cell or tissue type, might be abnormal for a different cell or tissue type.

As used herein, the term "about" will be understood by persons of ordinary skill in the art and will vary to some extent on the context in which it is used. As used herein when referring to a measurable value such as an amount, a concentration, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

By "alteration" or "change" is meant an increase or decrease. An alteration may be by at least about 1%, 2%, 3%, 4%, 5%, 10%, 20%, 30%, 40%, 50%, 60%, 70%, 75%, 80%, 90%, or 100%, or any fraction or multiple thereof.

As used herein, "animal" refers to living multi-cellular vertebrate organisms, a category that includes, for example, mammals and birds.

As used herein, "antibody" refers to a polypeptide ligand comprising at least a light chain or heavy chain immunoglobulin variable region that specifically binds an epitope of a protein or a fragment thereof. Antibodies can include a heavy chain and a light chain, each of which has a variable region, termed the variable heavy (VH) region and the variable light (VL) region. Together, the VH region and the VL region are responsible for binding the antigen recognized by the antibody. This includes intact immunoglobulins and the variants and portions of them well known in the art, such as Fab' fragments, F(ab)'2 fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes recombinant forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, IL); Kuby, Immunology, 3rd Ed., W.H. Freeman & Co., New York, 1997. A variety of immunoassay formats are appropriate for selecting antibodies specifically immunoreactive with a particular protein. For example, solid-phase ELISA immunoassays are routinely used to select monoclonal antibodies specifically immunoreactive with a protein. Also available are immunoprecipitation or immunoblotting assays. See Harlow & Lane, Antibodies, *A Laboratory Manual*, Cold Spring Harbor Publications, New York (1988), for a description of immunoassay formats and conditions that can be used to determine specific immunoreactivity An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations, κ and λ, light chains refer to the two major antibody light chain isotypes.

The term "antigen" or "Ag" as used herein is defined as a molecule that binds to a receptor of the immune system and provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequence or a partial nucleotide sequence encoding a protein that elicits an immune response, therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid. The term "protein antigens" as used herein includes protein and peptide antigens.

By the term "applicator," as the term is used herein, is meant any device including, but not limited to, a hypodermic syringe, a pipette, an iontophoresis device, a patch, and the like, for administering the compositions of the invention to a subject.

As used herein, the term "autoantibodies" refers to antibodies that are capable of reacting against an antigenic constituent of an individual's own tissue or cells (e.g., the antibodies recognize and bind to "self" antigens).

As used herein, "binding" refers to a specific interaction between two or more molecules, such as the binding of an antibody and an antigen (for example an antibody to an antigen). In certain embodiments, specific binding is identified by a dissociation constant (Kd). In other embodiments, binding affinity is calculated by a modification of the Scatchard method described by Frankel et al., 1979, Mol. Immunol. 16:101-106. In other embodiments, binding affinity is measured by an antigen/antibody dissociation rate. In yet other embodiments, a high binding affinity is measured by a competition radioimmunoassay (RIA). In several examples, a high binding affinity is at least about $1 \times 10^{-8}$M. In other embodiments, a high binding affinity is at least about $1.5 \times 10^{-8}$, at least about $2.0 \times 10^{-8}$, at least about $2.5 \times 10^{-8}$, at least about $3.0 \times 10^{-8}$, at least about $3.5 \times 10^{-8}$, at least about $4.0 \times 10^{-8}$, at least about $4.5 \times 10^{-8}$, or at least about $5.0 \times 10^{-8}$ M. In one example, the disclosed antibodies have a binding affinity for the antigen of at least 10 nM.

"Biological sample" or "sample" as used herein means a biological material isolated from an individual. The biological sample may contain any biological material suitable for detecting the desired biomarkers, and may comprise cellular and/or non-cellular material obtained from the individual. A biological sample may be of any biological tissue or fluid. Frequently the sample will be a "clinical sample," which is a sample derived from a patient. Typical clinical samples include, but are not limited to, bodily fluid samples such as synovial fluid, sputum, blood, urine, blood plasma, blood serum, sweat, mucous, saliva, lymph, bronchial aspirates, peritoneal fluid, cerebrospinal fluid, and pleural fluid, and tissues samples such as blood-cells (e.g., white cells), tissue or fine needle biopsy samples and abscesses or cells therefrom. Biological samples can also include sections of tissues, such as frozen sections or formalin fixed sections taken for histological purposes. In certain embodiments of the invention, the immunoglobulin-containing biological sample is serum, whole blood, CSF, saliva, or sputum. A blood sample can be obtained by methods known in the art including venipuncture or a finger stick. CSF can be obtained by methods known in the art including a lumbar spinal tap. To obtain serum from blood, a sample of blood is received and centrifuged at a speed sufficient to pellet all cells and platelets, and the serum to be analyzed is drawn from the resulting supernatant. Sputum and saliva samples can be collected by methods known in the art. The biological samples can be diluted with a suitable buffer before conducting the assay. In certain embodiments, the biological sample is serum or whole blood.

A "biomarker" or "marker" as used herein generally refers to a nucleic acid molecule, clinical indicator, protein, antibody, or other analyte that is associated with a disease. In certain embodiments, a marker is differentially present in a biological sample obtained from a subject having or at risk of developing a disease (e.g., MS) relative to a reference. A marker is differentially present if the mean or median level of the biomarker present in the sample is statistically different from the level present in a reference. A reference level may be, for example, the level present in an environmental sample obtained from a clean or uncontaminated source. A reference level may be, for example, the level present in a sample obtained from a healthy control subject or the level obtained from the subject at an earlier timepoint, i.e., prior to treatment. Common tests for statistical significance include, among others, t-test, ANOVA, Kruskal-Wallis, Wilcoxon, Mann-Whitney and odds ratio. Biomarkers, alone or in combination, provide measures of relative likelihood that a subject belongs to a phenotypic status of interest. The differential presence of a marker of the invention in a subject sample can be useful in characterizing the subject as having or at risk of developing a disease (e.g., MS), for determining the prognosis of the subject, for evaluating therapeutic efficacy, or for selecting a treatment regimen.

As used herein, a "biosensor" is an analytical device for the detection of an analyte in a sample. Biosensors can comprise a recognition element, which can recognize or capture a specific analyte, and a transducer, which transmits the presence or absence of an analyte into a detectable signal.

As used herein, the terms "comprising," "including," "containing" and "characterized by" are exchangeable, inclusive, open-ended and do not exclude additional, unrecited elements or method steps. Any recitation herein of the term "comprising," particularly in a description of components of a composition or in a description of elements of a device, is understood to encompass those compositions and methods consisting essentially of and consisting of the recited components or elements. As used herein, the term "consisting of" excludes any element, step, or ingredient not specified in the claim element. As used herein, the term "consisting essentially of" does not exclude materials or steps that do not materially affect the basic and novel characteristics of the claim.

As used herein, the term "contacting" includes in solution and solid phase, for example contacting a sample with an antibody, for example contacting a sample that contains an autoantibody of interest.

The term "control level" as used herein means a biomarker level in a sample from a subject where the subject does not have the condition being tested. The term "control level" is also construed herein to mean an average level of an endogenous biomarker in samples obtained from more than one subject where the subject does not have the condition being tested. Thus, as used herein, the term "endogenous biomarker" relates to naturally-occurring levels of a biomarker in a control sample such as in a control/normal/healthy individual. The term "control level" is also construed herein to mean a reference biomarker level obtained through calculation of what such a biomarker level might be in samples from a hypothetical group of subjects not having the condition being tested. In certain embodiments, the control level is therefore a level of biomarker against which a test level is measured. The control biomarker level can serve as a comparator against which a test sample can be compared.

As used herein, the term "data" in relation to one or more biomarkers, or the term "biomarker data" generally refers to data reflective of the absolute and/or relative abundance (level) of a product of a biomarker in a sample. As used herein, the term "dataset" in relation to one or more biomarkers refers to a set of data representing levels of each of one or more biomarker products of a panel of biomarkers in a reference population of subjects. A dataset can be used to generate a formula/classifier of the invention. According to one embodiment, the dataset need not comprise data for each biomarker product of the panel for each individual of the reference population. For example, the "dataset" when used in the context of a dataset to be applied to a formula can refer to data representing levels of products of each biomarker for each individual in one or more reference populations, but as would be understood can also refer to data representing levels of each biomarker for 99%, 95%, 90%, 85%, 80%, 75%, 70% or less of the individuals in each of the one or more reference populations and can still be useful for purposes of applying to a formula.

By "detectable moiety" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

As used herein, the terms "determining," "assessing," "assaying," "measuring," and "detecting" refer to both quantitative and qualitative determinations, and as such, the term "determining" is used interchangeably herein with "assaying," "measuring," and the like. Where a quantitative determination is intended, the phrase "determining an amount" of an analyte and the like is used. Where a qualitative and/or quantitative determination is intended, the phrase "determining a level" of an analyte or "detecting" an analyte is used.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The terms "effective amount" or "therapeutically effective amount" are used interchangeably herein, and refer to an amount of a compound, formulation, material, or composition, as described herein effective to achieve a particular biological result. Such results may include, but are not limited to, the treatment of a disease or condition as determined by any means suitable in the art.

"Immunoassay" refers to a biochemical test that measures the presence or concentration of a substance in a sample, such as a biological sample, using the reaction of an antibody to its cognate antigen, for example the specific binding of an antibody to a protein. Both the presence or the amount of antigen and/or antibody present can be measured or determined. Measuring the quantity of antigen can be achieved by a variety of methods. One of the most common is to label either the antigen or antibody with a detectable label.

An "individual", "patient" or "subject", as these terms are used interchangeably herein, includes a member of any animal species including, but are not limited to, birds, humans and other primates, and other mammals including commercially relevant mammals such as cattle, pigs, horses, sheep, cats, and dogs. Preferably, the subject is a human.

As used herein, the term "instructional material" includes a publication, a recording, a diagram, or any other medium of expression that can be used to communicate the usefulness of the compositions and methods of the invention. In some instances, the instructional material can be part of a kit useful for preparing and/or using a composition of the invention. The instructional material of the kit may, for example, be affixed to a container that contains the compositions of the invention or be shipped together with a container that contains the compositions. Alternatively, the instructional material can be shipped separately from the container with the intention that the recipient uses the instructional material and the compositions cooperatively. For example, the instructional material is for use of a kit; or instructions for use of a compound or composition of the invention.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

As used herein, a "label" is detectable compound or composition that is conjugated directly or indirectly to another molecule, such as an antibody or a protein, to facilitate detection of that molecule. Specific, non-limiting examples of labels include fluorescent tags, enzymatic linkages (such as horseradish peroxidase), radioactive isotopes (for example $^{14}C$, $^{32}P$, $^{125}I$, $^{3}H$ isotopes and the like) and particles such as colloidal gold. In some examples a protein, such as a protein associated with a fungus, is labeled with a radioactive isotope, such as $^{14}C$, $^{32}P$, 125I, $^{3}H$ isotope. In some examples an antibody that specifically binds the protein is labeled. Methods for labeling and guidance in the choice of labels appropriate for various purposes are discussed for example in Sambrook, et al., 1989, Molecular Cloning: *A Laboratory Manual*, Cold Spring Harbor, New York, 1989; Ausubel, et al., 1998, In Current Protocols in Molecular Biology, John Wiley & Sons, New York, 1998; Harlow & Lane, 1988, Antibodies, *A Laboratory Manual*, Cold Spring Harbor Publications, New York. Patents teaching the use of such labels include U.S. Pat. Nos. 3,817,837, 3,850,752, 3,939,350, 3,996,345, 4,277,437, 4,275,149 and 4,366,241, all of which are incorporated herein in their entireties by reference. Means of detecting such labels are well known to those of skill in the art. Thus, for example, radiolabels may be detected using photographic film or scintillation counters; fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label. Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, in U.S. Ser Nos. 10/389,194, 60/493,495 and in PCT Application PCT/US99/06097 (published as WO99/47964), all of which are incorporated herein in their entireties by reference.

The term "mammal" includes both human and non-human mammals.

By "marker profile" is meant a characterization of the signal, level, expression or expression level of two or more markers (e.g., antigens and/or autoantibodies).

By the term "microarray" is meant a collection of nucleic acid, protein, antigen, and/or antibody probes immobilized on a substrate. "DNA microarrays" (or "DNA chip(s)"), "RNA microarrays", "protein microarrays", and "antibody arrays" encompass all art-recognized solid supports, and all art-recognized methods for affixing nucleic acid, protein, antigen, and/or antibody molecules thereto or for synthesis of nucleic acids thereon and antibodies. Certain arrays typically comprise a plurality of different nucleic acid, protein, antigen, and/or antibody probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 5,800,992, 6,040,193, 5,424,186, and Fodor et al., 1991, Science, 251:767-777, each of which is incorporated by reference in its entirety for all purposes. Arrays may be used to assess large amounts of biological material using high-throughput screening miniaturized, multiplexed and parallel processing, and detection methods. Arrays may generally be produced using a variety of techniques, such as mechanical synthesis methods or light directed synthesis methods that incorporate a combination of photolithographic methods and solid phase synthesis methods. Techniques for the synthesis of these arrays using mechanical synthesis methods are described in, e.g., U.S. Pat. Nos. 5,384,261, and 6,040,193, all of which are incorporated herein by reference in their entirety for all purposes. Although a planar array surface is preferred, the array may be fabricated on a surface of virtually any shape or even a multiplicity of surfaces. Arrays may be antigens, nucleic acids or antibodies on beads, gels, polymeric surfaces, and fibers such as fiber optics, glass or any other appropriate substrate. See U.S. Pat. Nos. 5,770,358, 5,789,162, 5,708,153, 6,040,193 and 5,800,992, all of which are hereby incorporated by reference in their entirety for all purposes. Arrays may be packaged in such a manner as to allow for diagnostic use or can be an all-inclusive device; e.g., U.S. Pat. Nos. 5,856,174 and 5,922,591, all of which incorporated in their entirety by reference for all purposes. Arrays are commercially available from, for example, Affymetrix (Santa Clara, Calif.) and Applied Biosystems (Foster City, Calif.), and are directed to a variety of purposes, including genotyping, diagnostics, mutation analysis, marker expression, and gene expression monitoring for a variety of eukaryotic and prokaryotic organisms. The number of probes on a solid support may be varied by changing the size of the individual features. In certain embodiments the feature size is 20 by 25 microns square, in other embodiments features are, for example, 8 by 8, 5 by 5, or 3 by 3 $\mu m^2$, resulting in about 2,600,000, 6,600,000 or 18,000,000 individual probe features.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. These fused cells and their progeny are termed "hybridomas." Monoclonal antibodies include humanized monoclonal antibodies By "reference" is meant a standard of comparison. As is apparent to one skilled in the art, an appropriate reference is where an element is changed in order to determine the effect of the element. In certain embodiments, the level of a target nucleic acid molecule present in a sample may be compared to the level of the target nucleic acid molecule present in a clean or uncontaminated sample. For example, the level of a target nucleic acid molecule present in a sample may be compared to the level of the target nucleic acid molecule present in a corresponding healthy cell or tissue or in a diseased cell or tissue (e.g., a cell or tissue derived from a subject having a disease, disorder, or condition).

As used herein, the term "sample" includes a biologic sample such as any tissue, cell, fluid, or other material derived from an organism.

The term "solid support," "support," and "substrate" as used herein are used interchangeably and refer to a material or group of materials having a rigid or semi-rigid surface or surfaces. In certain embodiments, at least one surface of the solid support is substantially flat, although in certain embodiments it is desirable to physically separate synthesis regions for different compounds with, for example, wells, raised regions, pins, etched trenches, or the like. According to other embodiments, the solid support(s) take(s) the form of beads, resins, gels, microspheres, microplates, or other geometric configurations. See U.S. Pat. No. 5,744,305, which is hereby incorporated by reference in its entirety for all purposes.

By the term "specifically binds," as used herein, is meant a molecule, such as an antibody or a small molecule, which recognizes and binds to another molecule or feature, but does not substantially recognize or bind other molecules or features in a sample.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology available and well known in the art.

As used herein, "therapeutic agent" refers to a substance that demonstrates some therapeutic effect by restoring or maintaining health, such as by alleviating the symptoms associated with a disease or physiological disorder, or delaying (including preventing) progression or onset of a disease. In some instances, the therapeutic agent is a chemical or pharmaceutical agent, or a prodrug. A therapeutic agent can be an agent that prevents or inhibits one or more signs or symptoms or laboratory findings associated with is disease contemplated in the invention. In certain embodiments, the therapeutic agent comprises intravenous corticosteroids, such as methylprednisolone, interferon beta-la, interferon beta-1b, glatiramer acetate, mitoxantrone, natalizumab, fingolimod, teriflunomide, dimethyl fumarate, alemtuzumab, rituximab, and/or ocrelizumab.

The term "therapeutic intervention" as used herein means a treatment of a patient designed to alleviate a symptom experienced by the patient. The term should be construed to include surgical intervention. In certain embodiments, the therapeutic intervention comprises dietary supplementation and regimens, vitamin D, relaxation techniques such as yoga, herbal medicine (including medical *cannabis*), hyperbaric oxygen therapy, self-infection with hookworms, reflexology, acupuncture, and mindfulness.

A "therapeutically effective amount" or "effective amount" or "therapeutically effective dose" is that amount or dose sufficient to inhibit or prevent onset or advancement, to treat outward symptoms, or to cause regression, of a disease. The therapeutically effective amount or dose also can be considered as that amount or dose capable of relieving symptoms caused by the disease. The therapeutically effective amount may vary depending the subject and disease condition being treated, e.g., the weight and age of the subject, the severity of the disease condition, the manner of administration and the like, which can readily be determined by one of ordinary skill in the art.

As used herein, the terms "treatment" and "treating" refer to an approach for obtaining beneficial or desired results including, but not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Disclosure

Due to the autoimmune nature of MS, much research attention has focused on specific components of the immune system to attempt to identify and diagnose patients at the earliest possible stage of their disease. For instance, autoantibodies targeting myelin surface proteins, such as myelin oligodendrocyte glycoprotein, myelin basic protein, myelin proteolipid protein, and myelin-associated glycoprotein, have demonstrated either associative or correlative links to MS, however, they currently lack utility as accurate diagnostic biomarkers. Other autoantibody targets of growing interest are glycans, and include anti-GAGA4 or anti-glucose antibodies, as well as other cell surface ion channel proteins like KIR4.1. Despite the abundance of potential biomarker candidates, there is as of yet no definitive biofluid test capable of accurately diagnosing MS or monitoring its progression.

In one aspect, the present invention relates to the identification of autoantibodies that can be used to diagnose individuals with MS. Such diagnosis can use sera from MS subjects afflicted with either the relapsing-remitting MS (RRMS) or secondary progressive MS (SPMS) subtype, the two most prevalent clinical courses of this disease. Roughly 80% of all MS patients are initially diagnosed with RRMS and, during the course of their disease, more than 60% will transition to SPMS.

Sera from a total of 112 subjects were analyzed, including 51 mixed-MS patients diagnosed with either RRMS or SPMS, the two most prevalent MS subtypes that together constitute the vast majority of all diagnosed cases. As demonstrated herein, a panel of blood-borne autoantibody biomarkers can be used to differentiate patients with MS from appropriate age- and gender-matched control subjects with an overall accuracy of 95.0%. Also identified were additional autoantibody biomarker panels that are subtype-specific for RRMS or SPMS, and the use each of these panels to successfully differentiate between each MS subtype has been demonstrated. Using RRMS-specific autoantibody biomarkers, it was possible to differentiate RRMS patients from SPMS patients with 100.0% accuracy. Similarly, SPMS-specific autoantibody biomarkers were capable of differentiating SPMS patients from RRMS patients with 92.0% accuracy. In other words, subtype-specific autoantibody biomarker panels and their corresponding diagnostic logic were capable of successfully differentiating between RRMS and SPMS, two clinically relevant MS subtypes representing two discrete phases of the same disease. These comparisons demonstrate the potential of autoantibody biomarker panels to effectively and sequentially stage the clinical course of MS, as well as to predict the point of transition between subtypes. MS subjects were also readily distinguished with comparable accuracy from those with breast cancer, a non-neurodegenerative disease, used as a disease control group.

As demonstrated herein, human protein microarrays provide an accurate and reliable platform for the discovery of blood-based autoantibodies that serve as powerful diagnostic indicators or biomarkers of ongoing MS disease. The strength in this unconventional approach to MS and other disease diagnostics lies in the role, as presently understood, of autoantibodies in the maintenance of body-wide homeostasis through clearance of tissue debris produced in response to ongoing pathology. The present biomarker discovery strategy has focused on identifying differentially expressed autoantibodies in disease groups relative to healthy control subjects. Using this approach it is not only possible to diagnose and stage early phases of both of these diseases, but also to differentiate them from other closely related neurological diseases with high overall accuracy.

The autoantibody biomarker panel used herein to distinguish MS patients from matched controls (Table 1) comprises a wide variety of constituent proteins, but lacks confirmation of previously described targets of interest. Identified biomarkers include dehydrogenases, regulatory proteins, voltage-gated potassium channel subunits, kinases, and transcription factors, among others. Without wishing to be bound by any particular theory, based on knowledge currently available some proposed functions of these selected biomarkers include neuronal differentiation, nerve signal regulation, innate immunity processes, cell motility, RNA modification, transcription/translation regulation, and glycolipid biosynthesis. Although much research effort in the field of MS has previously concentrated on autoantibodies to specific myelin components as biomarkers of the disease, results thus far have been disappointing. The present disclosure demonstrates that shifting towards including a variety of antibodies to other proteins as potential biomarkers is important to accurate MS diagnosis and typing.

In previous studies detailing the discovery and testing of blood-based autoantibody biomarkers with utility for diagnosing and staging of Alzheimer's and Parkinson's disease, the most useful biomarkers selected were observed to be autoantibodies exhibiting a higher titer in diseased subjects than in controls. Without wishing to be bound by any particular theory, this pattern coincided with the concept that these autoantibodies are produced in response to debris emanating from regions of pathology and enter the blood, implying a function for autoantibodies in the clearance of such debris from the blood. Such biomarkers would be useful for disease monitoring in patients under treatment by their physicians or in clinical trials, where a beneficial effect would coincide with reduction in debris production from the region of pathology as well as a corresponding reduction in the titers of autoantibodies charged with their clearance. In stark contrast, the present disclosure relating to MS indicates that autoantibodies with lower or depleted titers were found to be the most sensitive, accurate and thus useful biomarkers for disease diagnosis. Without wishing to be bound by any particular theory, this indicates that the binding of certain autoantibodies to available targets in regions associated with MS pathology is driving their selective depletion, and is also playing a causal role in MS.

Brain-reactive autoantibodies are ubiquitous in human blood and, under conditions of blood-brain barrier compromise, such autoantibodies gain access to the brain interstitium and can bind to exposed targets on the surfaces of neurons and glia. Indeed, in the brains of patients with Alzheimer's disease, the same neurons showing particular vulnerability to AD pathological changes, including intraneuronal beta-amyloid deposition, are also the cells that are most immunoglobulin G-positive. Without wishing to be bound by any particular theory, chronic IgG binding to neuronal surfaces under conditions of blood-brain barrier breach can possibly play a role in AD pathological changes and facilitate amyloid deposition in the affected brain.

Again, without wishing to be bound by any particular theory, the same type of mechanism can be possibly operating in MS patients, where transient or chronic access of autoantibodies to their targets on the myelin sheath or axonal membranes at the node of Ranvier contribute to a dampening or blocking of nerve impulse transmission at the affected region. The factors precipitating intervals of access of autoantibodies to neuronal targets can involve, in a non-limiting example, transient increases in blood-brain barrier permeability.

In one aspect, the present invention describes a diagnostic approach to MS that employs only a small volume of a biological fluid (such as blood), is relatively non-invasive, and independent of diagnostic imaging, such as MM. In another aspect, the present invention provides separate panels of autoantibody biomarkers to distinguish between RRMS and SPMS, two clinically distinct subtypes with distinctive pathological disease courses. Again, without wishing to be bound by any particular theory, this finding supports the hypothesis that autoantibody profiles can change with the progression of disease, with each disease and disease stage having its own unique autoantibody signature or profile. If autoantibody profiles are responsive to and reflect disease-associated cell and tissue debris production or the initial binding of brain-reactive autoantibodies to newly available targets as a result of blood-brain barrier compromise, this information can be useful for determining which profile changes might indicate whether or not a patient will progress or has progressed from one stage to the next, such as the transition from RRMS to SPMS.

The present disclosure is directed to the disclosed diagnostic strategy using autoantibody biomarkers that can be used to detect MS and differentiate between different clinical MS subtypes, as well as distinguish MS subjects from those with early-stage PD, a closely related neurodegenerative disorder, albeit with lower accuracy.

The present disclosure is thus directed to a sensitive and specific test for the general diagnosis of MS and two of its subtypes. MS represents a wide range of symptoms, clinical presentations, and natural histories, and thus encompasses a truly heterogeneous patient population—conditions that can often complicate a straightforward diagnosis. The course and progression of the disease is dependent on early and accurate diagnoses, followed by treatment intervention. Patients will undoubtedly benefit from earlier, more accurate diagnosis and monitoring throughout the course of their disease. Based on the present disclosure, a well-developed, readily accessible and affordable diagnostic tool is available to enable progress in the fields of MS research and treatment. The presently disclosed diagnostic blood test are useful in differentiating between a patient experiencing a clinically isolated syndrome triggered by MS, and one that is due to other causes. In addition, such diagnostic has utility as a screening tool that allows physicians to appropriately direct their patients to seek additional confirmatory tests for MS. The present diagnostic strategy can also be applicable to verify early enrollment of patients into clinical trials, as well as serve as a means to monitor a patient's response to a particular treatment regimen through documentation of the subsequent loss of MS-relevant biomarkers. Thus, such diagnostic tool can allow a physician to monitor disease progression while the patient is under treatment. If the treatment is working, the biomarkers will drop out and become undetectable compared to earlier test results, thereby providing a biochemical confirmation that the treatment is working to alleviate the disease. It can also be used as a prognostic indicator of impending MS relapses or worsening conditions/disease progression, as well as the transition between MS clinical subtypes.

Assaying Autoantibodies:

Methods for assaying autoantibodies are described herein in and known to those of ordinary skill in the art. For example, an immunoassay can be used to detect and analyze autoantibodies in a biological sample. As used herein, the term "immunoassay" is used in reference to any method in which an antibody is used in the detection of an antigen, or in which an antigen is used in the detection of an antibody, thus forming an immunocomplex.

The antigens recited herein are identified by art-accepted names as well as database identification numbers. The database identification numbers refer to the publically available protein databases of the National Center for Biotechnology Information (NCBI), which are well-known and accessible to those of ordinary skill in the art.

It is contemplated that a range of immunoassay formats be encompassed by this definition, including but not limited to, competition assays, direct immunoassays, indirect immunoassays, and "sandwich immunoassays." However, it is not intended that the present invention be limited to any particular format. It is contemplated that other formats, including radioimmunoassays (RIA), immunofluorescent assays (IFA), and other assay formats, including, but not limited to, variations on the ELISA, RIA and/or IFA methods are useful in the methods of the present invention. Immunoassay also includes immunoprecipitation and/or immunoblotting.

Assays for the detection of immunocomplexes may be quantitative or qualitative. In certain embodiments, the assay utilizes a solid phase or substrate to which the autoantigens are directly or indirectly attached, such as a microtiter or microassay plate, slide, magnetic bead, non-magnetic bead, column, matrix, membrane, or sheet, and can be composed of a synthetic material such as polystyrene, polyvinyl chloride, polyamide, or other synthetic polymers, natural polymers such as cellulose, derivatized natural polymers such as cellulose acetate or nitrocellulose, and glass, for example glass fibers. The substrate can comprise a plurality of individually addressable autoantigens immobilized on the surface. The individually addressable autoantigens can be immobilized on the surface to form an array. The substrates can be used in suitable shapes, such as films, sheets, or plates, or may be coated onto or bonded or laminated to appropriate inert carriers, such as paper, glass, plastic films, or fabrics. In other embodiments, the substrate is a slide or a bead.

In one aspect, the methods of the present invention include using a sandwich assay to detect the autoantibodies contemplated in the invention. The assays and peptides described herein are applicable to any proteins/peptides/biomarkers described herein, isoforms thereof, post-translationally modified forms thereof, or combinations of any of the foregoing. Sandwich assays generally involve the use of two binding agents, e.g., antibodies, each capable of binding to a different portion, or epitope, of the protein(s) to be detected and/or quantitated. In a sandwich assay, the analyte is typically bound by a first binding agent that is immobilized on a solid support, and thereafter a second binding agent binds to the analyte, thus forming an insoluble complex. See, e.g., U.S. Pat. No. 4,376,110, which is incorporated herein in its entirety by reference. Alternatively, the sandwich assay may be performed in solution, also referred to as a homogeneous assay. See, e.g., U.S. Pat. No. 7,413,862, which is incorporated herein in its entirety by reference.

In certain embodiments, a capture probe including a first binding agent is capable of specifically binding to a MS-associated antigen, which bound to one or more autoantibodies. In turn, the detection probe including a second binding agent binds to the autoantibodies. Thus, in this particular example, a four-part complex is formed between: (1) the capture probe, (2) the disease-associated antigen, (3) the autoantibody, and (4) the detection probe. In other embodiments, the positions of the first and second binding agents are reversed, such that the capture probe attached to the solid support is capable of specifically binding to the autoantibodies and the detection probe is capable of specifically binding to the MS-associated antigen.

In a non-limiting example, an appropriate capture probe is immobilized on a solid surface and the sample to be tested (e.g., human serum) is brought into contact with the capture probe. For example, modified glass substrates that covalently or non-covalently bind proteins can be used to bind the disease-associated antigen. The substrate may be treated with suitable blocking agents to minimize non-specific binding. If the autoantibody is present in the sample, a complex between the autoantibody and the capture probe is formed. A detection probe is then added, which specifically recognizes an epitope of a human immunoglobulin (Ig), if present. The anti-human immunoglobulin detection probe can be directed against the Fc region of the human antibody and with as little cross-reactivity as possible against the capture antibody species.

In another non-limiting example, a sample from the subject is contacted with a capture probe including an antibody capable of binding to a disease-associated antigen. The sample is also contacted with a detection probe including anti-human Ig antibodies. The presence, absence, and/or amount of the complex can be detected, wherein the presence or absence of the complex is indicative of the presence or absence of the autoantibodies.

The immunocomplex can then be detected or quantitatively measured using methods well-known in the art, including label-based and label-free detection. Indicator reagents include chromogenic agents, catalysts such as enzyme conjugates, fluorescent compounds such as fluorescein and rhodamine, chemiluminescent compounds such as dioxetanes, acridiniums, phenanthridiniums, ruthenium, and luminol, radioactive elements, direct visual labels, as well as cofactors, inhibitors and magnetic particles. Examples of enzyme conjugates include alkaline phosphatase (AP), horseradish peroxidase (HRP), and beta-galactosidase. For example, one can use a secondary antibody that is coupled to an indicator reagent comprising a signal generating compound. The secondary antibody can be an anti-human IgG antibody. Detection of the complex can be achieved by the addition of a substrate for the enzyme which generates a calorimetric, chemiluminescent or fluorescent product. Alternatively, the presence of the complex can be determined by addition of a marker protein labeled with a detectable label, for example an appropriate enzyme. In this case, the amount of enzymatic activity measured is inversely proportional to the quantity of complex formed, and a negative control is needed as a reference to determine the presence of antigen in the sample. Another method for detecting the complex can utilize antibodies or antigens that have been labeled with radioisotopes followed by measure of radioactivity.

In certain exemplary embodiments, fluorescence labeling and detection methods are used to detect the immunocomplexes. Commercially available slide scanners (e.g. the Genepix 4000B slide scanner (Molecular Devices, Inc.) with associated analytical software may be used. In other embodiments, the immunocomplex is probed with fluorescent-labeled (e.g., Alexa-Fluor (Invitrogen)) anti-human antibody and the intensity of fluorescence at each protein spot is measured using a microarray scanner. Commercially available software (e.g. GenePix Pro 5.0 software (Axon instruments)) can be used to extract the net median pixel intensities for individual features from the digital images produced by the scanner. Data can be normalized by comparing median values of multiple identical control spots in different regions of the same array.

Methods of label-free detection include surface plasmon resonance, carbon nanotubes and nanowires, and interferometry. Label-based and label-free detection methods are known in the art, e.g., by Ray, et al., 2010, Proteomics 10:731-748, which is incorporated herein in its entirety by reference. Detection can be accomplished by scanning methods known in the art and appropriate for the label used, and associated analytical software.

The sample can be contacted with the detection probe before, after, or simultaneously with the capture probe. In one embodiment, the sample is first contacted with the detection probe so that autoantibodies present in the sample bind to the detection probe to form a target analyte complex. The mixture is then contacted with the substrate having capture probes bound thereto so that the target analyte complex binds to the capture probe on the substrate. In another embodiment, the sample is first contacted with the substrate so that a target analyte complex present in the sample binds to a capture probe, and the target analyte complex bound to the capture probe is then contacted with the detection probe so that the autoantibodies bind to the detection probe. In another embodiment, the sample, the detection probe and the capture probe on the substrate are contacted simultaneously.

The present invention further provides kits for commercial sale. In certain embodiments, the kit can comprise at least one antigen contemplated in the invention. The kit can comprise the equipment, solutions and and/or instructions necessary for all steps in the process of creating any antigen contemplated in the invention, detecting autoantibodies contemplated in the invention, and the like. Furthermore, the kit can further comprise antigen(s) contemplated in the invention, isoforms thereof, post-translationally modified forms thereof, for use in detecting autoantibodies thereto.

Microarrays:

In certain aspects of the invention, a sample is analyzed by means of a microarray. The antigens of the invention are useful as array elements in a microarray. Microarrays generally comprise solid substrates and have a generally planar surface, to which a capture reagent (also called an adsorbent or affinity reagent) is attached. Frequently, the surface of a biochip comprises a plurality of addressable locations, each of which has the capture reagent bound there.

The microarray of the invention can comprise any of the autoantigens recited herein, or a polypeptide or peptide fragment thereof containing one or more epitopes recognized by the MS diagnostic biomarker, or an epitope peptidomimetic that is recognized by the MS diagnostic biomarker. Peptidomimetics include, for example, D-peptides, peptoids, and β-peptides.

The array elements are organized in an ordered fashion such that each element is present at a specified location on the substrate. Useful substrate materials include membranes, composed of paper, nylon or other materials, filters, chips, glass slides, and other solid supports. The ordered arrangement of the array elements allows binding/recognition patterns and intensities to be interpreted as expression levels of particular genes or proteins (such as autoantibodies). Methods for making nucleic acid microarrays are known to the skilled artisan and are described, for example, in U.S. Pat. No. 5,837,832, Lockhart, et al., 1996, Nat. Biotech. 14:1675-1680, and Schena, et al., 1996, Proc. Natl. Acad. Sci. 93:10614-10619, herein incorporated by reference in their entireties by reference. Methods of forming high-density arrays of nucleic acids, peptides, and other polymer sequences with a minimal number of synthetic steps are known. The antigen array can be synthesized on a solid substrate by a variety of methods, including, but not limited to, light-directed chemical coupling, and mechanically directed coupling. See U.S. patent application Ser. Nos 10/658,879, 60/417,190, 09/381,480, and 60/409,396, and U.S. Pat. Nos. 5,861,242, 6,027,880, 5,837,832, and 6,723, 503, herein incorporated by reference in their entireties by reference.

Protein microarrays are known in the art and reviewed for example by Hall, et al., 2007, Mech Ageing Dev 128:161-167 and Stoevesandt, et al., 2009, Expert Rev Proteomics 6:145-157, the disclosures of which are incorporated herein by reference. Microarrays can be prepared by immobilizing purified autoantigens on a substrate such as a treated microscope slide using a contact spotter or a non-contact microarrayer. Microarrays can also be produced through in situ cell-free synthesis directly from corresponding DNA arrays. In certain embodiments, the autoantigens are coated or spotted onto the support or substrate such as chemically derivatized glass.

Methods for attaching the autoantigens to the support or substrate are known in the art and include covalent and noncovalent interactions. For example, diffusion of applied proteins into a porous surface such a hydrogel allows noncovalent binding of unmodified protein within hydrogel structures. Covalent coupling methods provide a stable linkage and may be applied to a range of proteins. Biological capture methods utilizing a tag (e.g., hexahistidine/Ni-NTA or biotin/avidin) on the protein and a partner reagent immobilized on the surface of the substrate provide a stable linkage and bind the protein specifically and in reproducible orientation.

For most applications, washing steps that follow binding will also vary in stringency. Wash stringency conditions can be defined by salt concentration and by temperature. As above, wash stringency can be increased by decreasing salt concentration or by increasing temperature. Stringent temperature conditions for the wash steps will ordinarily include a temperature of at least about 25° C., more preferably of at least about 42° C., and even more preferably of at least about 68° C. Additional variations on these conditions will be readily apparent to those skilled in the art. The microarray can be a biochip, or on a glass slide, bead, or paper.

Autoantigens:

The invention contemplates autoantigens recited herein, or a polypeptide or peptide fragment thereof containing one or more epitopes recognized by the MS diagnostic biomarker, or an epitope peptidomimetic that is recognized by the MS diagnostic biomarker. Peptidomimetics include, for example, D-peptides, peptoids, and β-peptides. The autoantigens can be purified from natural sources, or produced recombinantly or synthetically by methods known in the art, and can be in the form of fusion proteins. The autoantigens can be produced in vitro using cell-free translation systems. In certain embodiments, the autoantigens are produced in a mammalian or insect expression system to ensure correct folding and function. All of these methods can be automated for high throughput production.

Suitable methods for external production and purification of autoantigens to be spotted on arrays include expression in bacteria (as disclosed for example by Venkataram, et al., 2008, Biochem. 47:6590-6601), in yeast (as disclosed for example by Li, et al., 2007, Appl. Biochem. Biotechnol. 142:105-124), in insect cells (as disclosed for example by Altman, et al., 1999, Glycoconj. J. 16:109-123), and in mammalian cells (as disclosed for example by Spampinato, et al., 2007, Curr. Drug Targets 8:137-146).

Suitable methods for in situ ("on-chip") protein production are disclosed, for example, by Ramachandran, et al., 2006, Methods Mol. Biol 2328:1-14, and He, et al., 2008, Curr. Opin Biotechnol 19:4-9.

Other methods by which proteins are simultaneously expressed and immobilized in parallel on an array surface are also known in the art and may be used in accordance with the present invention. For example, in the Protein In Situ Arrays (PISA) method (He, et al., 2001, Nucleic Acids Res. 29:e73), proteins are made directly from DNA, either in solution or immobilized, and become attached to the array surface as they are made through recognition of a tag sequence. The proteins are expressed in parallel in vitro utilizing a cell free system, commonly rabbit reticulocyte or E. coli S30, to perform coupled transcription and translation. In this method, protein expression is performed on a surface which is precoated with an immobilizing agent capable of binding to the tag. Thus after each protein is translated, it becomes fixed simultaneously and specifically to the adjacent surface, while the other materials can subsequently be washed away. Microarrays are produced directly onto glass slides, either by mixing the DNA with the cell free lysate system before spotting or by a multiple spotting technique (MIST) in which DNA is spotted first followed by the expression system.

In the system known as Nucleic Acid Programmable Protein Array (NAPPA) (Ramachandran, et al., 2004, Science 305:86-90), transcription and translation from an immobilized (as opposed to a solution) DNA template allow conversion of DNA arrays to protein arrays. In this method, biotinylated cDNA plasmids encoding the proteins as GST fusions are printed onto an avidin-coated slide, together with an anti-GST antibody acting as the capture entity. The cDNA array is then covered with rabbit reticulocyte lysate to express the proteins, which become trapped by the antibody adjacent to each DNA spot, the proteins thereby becoming immobilized with the same layout as the cDNA. This technology generates a protein array in which the immobilized proteins are present together with DNA and a capture agent.

Another suitable method for generating a protein array is the DNA Array to Protein Array (DAPA) method. This method for in situ protein arraying uses an immobilized DNA array as the template to generate 'pure' protein arrays on a separate surface from the DNA, and also can produce multiple copies of a protein array from the same DNA template (He, et al., 2008, Nature Methods, 5:175-7). Cell-free protein synthesis is performed in a membrane held between two surfaces (e.g., glass slides), one of which is arrayed with DNA molecules while the other surface carries a specific reagent to capture the translated proteins. Individual, tagged proteins are synthesized in parallel from the arrayed DNA, diffuse across the gap and are subsequently immobilized through interaction with the tag-capturing reagent on the opposite surface to form a protein array. Discrete spots which accurately reflect the DNA in position and quantity are produced. Replicate copies of the protein array can be obtained by reuse of the DNA.

Array fabrication methods include robotic contact printing, ink-jetting, piezoelectric spotting and photolithography. For example, purified autoantigens of the invention that are produced and purified externally can be spotted onto a microarray substrate using a flexible protein microarray inkjet printing system (e.g., ArrayJet, Roslin, Scotland, UK) to provide high quality protein microarray production. The precise rows and columns of autoantigens can be converted to detectable spots denoting both the presence and amount of serum diagnostic biomarkers that have been bound.

The production of the microarrays is preferably performed with commercially available printing buffers designed to maintain the three-dimensional shape of the autoantigens. In certain embodiments, the substrate for the microarray is a nitrocellulose-coated glass slide.

Biosensors:

In certain embodiments, the biomarkers of the invention are detected using biosensors, e.g. with sensor systems with amperometric, electrochemical, potentiometric, conductimetric, impedance, magnetic, optical, acoustic or thermal transducers.

Generally, biosensors include a biosensor recognition element that can include proteins, nucleic acids, antibodies, and so forth, that bind to a particular biomarker and a transducer that converts a molecular signal (i.e. binding of biomarker to recognition element) into an electric or digital signal that can be quantified, displayed, and analyzed. Biosensors can also include a reader device that translates the signal into a user-friendly display of the results. Examples of potential components that comprise an exemplary biosensor are described in Bohunicky et al., 2011, Nanotechnology Science and Applications 4:1-10, which is hereby incorporated by reference in its entirety.

A biosensor can incorporate a physical, chemical or biological detection system. In certain embodiments, a biosensor is a sensor with a biological recognition system, e.g. based on a nucleic acid, such as an oligonucleotide probe or aptamer, or a protein such as an enzyme, binding protein, receptor protein, transporter protein or antibody. In other embodiments, the biological recognition system can comprise traditional immunoassays described elsewhere herein. In yet other embodiments, the recognition element (e.g. protein, nucleic acid, antibody, etc.) can be unlabeled and binding of the biomarker to the element is directly observed and converted into a signal by the transducer. A biosensor can include microfluidic means for measuring or dispensing volumes, housing reagents causing mixing, providing incubation by capillary flow, gravity, electro-motive force or other means to move fluid.

The method for detection of the biomarker in a biosensor uses immunological, electrical, thermal, magnetic, optical (e.g. hologram) or acoustic technologies. Using such biosensors, it is possible to detect the target biomarker at the anticipated concentrations found in biological samples.

The biosensor can incorporate detection methods and systems as described herein for detection of the biomarker. Biosensors can employ electrical (e.g. amperometric, potentiometric, conductimetric, or impedance detection systems), calorimetric (e.g. thermal), magnetic, optical (e.g. hologram, luminescence, fluorescence, colorimetry), or mass change (e.g. piezoelectric, acoustic wave) technologies. In a biosensor according to the invention the level of one, two, three, or more biomarkers can be detected by one or more methods selected from: direct, indirect or coupled enzymatic, spectrophotometric, fluorimetric, luminometric, spectrometric, polarimetric and chromatographic techniques. Certain biosensors comprise one or more enzymes used directly or indirectly via a mediator, or using a binding, receptor or transporter protein, coupled to an electrical, optical, acoustic, magnetic or thermal transducer. Using such biosensors, it is possible to detect the level of target biomarkers at the anticipated concentrations found in biological samples.

In certain embodiments, a biomarker of the invention can be detected using a biosensor incorporating technologies based on "smart" holograms, or high frequency acoustic systems, such systems are particularly amenable to "bar code" or array configurations. In smart hologram sensors (Smart Holograms Ltd, Cambridge, UK), a holographic image is stored in a thin polymer film that is sensitized to react specifically with the biomarker. On exposure, the biomarker reacts with the polymer leading to an alteration in the image displayed by the hologram. The test result readout can be a change in the optical brightness, image, color and/or position of the image. For qualitative and semi-quantitative applications, a sensor hologram can be read by eye, thus removing the need for detection equipment. A simple color sensor can be used to read the signal when quantitative measurements are required. Opacity or color of the sample does not interfere with operation of the sensor. The format of the sensor allows multiplexing for simultaneous detection of several substances. Reversible and irreversible sensors can be designed to meet different requirements, and continuous monitoring of a particular biomarker of interest is feasible.

Biosensors to detect the biomarker of the invention can include acoustic, surface plasmon resonance, holographic, and/or microengineered sensors. Imprinted recognition elements, thin film transistor technology, magnetic acoustic resonator devices, and other novel acousto-electrical systems can be employed in biosensors for detection of the biomarkers of the invention.

Suitably, biosensors for detection of the biomarker of the invention are coupled, i.e. they combine biomolecular recognition with appropriate means to convert detection of the presence, or quantitation, of the biomarker in the sample into a signal. Biosensors can be adapted for "alternate site" diagnostic testing, e.g. in the ward, outpatients' department, surgery, home, field and workplace.

The present invention further contemplates a computing system having an autoantigen database and software algorithm stored in a non-transitory computer readable medium. In certain embodiments, the computing system is configured to generate a report identifying the risk of a subject in developing MS, or a sub-type thereof, as based on formation (or not) of immunocomplexes between an autoantigen and an autoantibody in a biological sample from a subject, as recited in the present disclosure. Based on the common knowledge in the field, one skilled in the art of computer system would know how to identify a computing system that is properly configured to receive the results of whether an immunocomplex between an autoantigen and an autoantibody is formed, and determine that, if that immunocomplex is indeed formed, that the subject has or is at risk of developing MS, or a sub-type thereof.

Treatment of MS, and the RRMS and SPMS subtypes of MS:

One aspect of the present invention includes methods of improving patient treatment outcomes by customizing patient's treatment regimen. There are several immunosuppressant medications approved for the treatment and management of both relapsing and progressive forms of MS. Disease-modifying treatments (DMTs) are the most commonly prescribed medications for relapsing-remitting and progressive MS patients that experience relapses, and are intended to reduce disease activity, lessen the severity of exacerbations, as well as slow progression, through various mechanisms of immunosuppression. DMTs include medications such as interferons, which are considered optimal first-line treatments for patients early in their disease course, and other therapies such as monoclonal antibodies, which are generally reserved for second- and third-line treatments due to safety concerns. Patients that do not respond to, or experience significant disease breakthrough while on first-line medications can be prescribed second- and third-line DMTs to better manage their specific disease course. For severe exacerbations, short-term high-dose corticosteroids are used to suppress the immune system, with the goal of shortening the duration of the relapse.

In addition to the treatments mentioned above for MS, many patients also use other medications to treat individual symptoms associated with the disease, such as pain, fatigue, depression, and bowel and bladder dysfunction. Because it is critical to begin first-line treatments as early as possible in a patient's disease course to attempt to slow progression and reduce relapse frequency and severity, it is of paramount importance to diagnose MS in the earliest stages of the disease. Currently, there is no single definitive test for the diagnosis and detection of MS. Patients often undergo a battery of tests involving neurologic exams, expensive diagnostic imaging, and invasive procedures, such as spinal fluid collection, so that a physician can rule out the possibility of other diseases. The implementation of a simple diagnostic blood test utilizing autoantibody biomarkers for the detection and diagnosis of MS is independent of diagnostic imaging, and negates the need for invasive procedures such as lumbar puncture. Furthermore, the high sensitivity of the blood test establishes the potential not only for early detection, but also for the differentiation between the RRMS and SPMS clinical subtypes. This allows for more precise management of a patient's disease course with regard to first-line treatments and beyond, as well as monitoring of the patient's response to specific therapies.

TABLE 1

Top 50 depleted markers.
Description of the top 50 depleted mixed-MS biomarkers.

| Database ID | Description |
| --- | --- |
| BC099907.1 | General transcription factor II-I |
| NM_201998.1 | Splicing factor 1 |
| BC028006.1 | inducible T-cell co-stimulator (ICOS) |
| NM_020317.2 | chromosome 1 open reading frame 63 (C1orf63) |
| NM_003636.1 | potassium voltage-gated channel, shaker-related subfamily, beta member 2 (KCNAB2), transcript variant 1 |
| BC003065.1 | Cell division protein kinase 2 |
| NM_001008737.1 | hypothetical LOC401052 (LOC401052) |
| XM_003960444.1 | Hypothetical protein MGC21881 (MGC21881), mRNA |
| BC029796.1 | hypothetical protein BC014011 (LOC116349) |
| NM_152716.1 | FLJ36874 protein (FLJ36874) |
| XM_379114.1 | hypothetical protein LOC150577 (LOC150577) |
| BC022258.1 | von Willebrand factor (VWF) |
| BC002733.2 | chromosome 1 open reading frame 77 (C1orf77) |
| NM_004912.1 | KRIT1, ankyrin repeat containing (KRIT1), transcript variant 2 |
| BC001419.1 | mitochondrial trans-2-enoyl-CoA reductase (MECR) |
| NM_002642.1 | Phosphatidylinositol N-acetylglucosaminyltransferase subunit C |
| PV4202 | NIMA (never in mitosis gene a)-related kinase 1 (NEK1) |
| PV4337 | LIM domain kinase 1 |
| XM_378514.1 | PREDICTED: *Homo sapiens* hypothetical protein LOC283663 (LOC283663), mRNA |
| XM_086879.4 | PREDICTED: *Homo sapiens* hypothetical LOC150371 (LOC150371) |
| BC015514.1 | tissue factor pathway inhibitor (lipoprotein-associated coagulation inhibitor) (TFPI) |
| NM_005151.2 | ubiquitin specific peptidase 14 (tRNA-guanine transglycosylase) (USP14), transcript variant 1 |
| BC016380.1 | cDNA clone MGC:27376 IMAGE:4688477, complete cds |
| BC032451.1 | cDNA clone MGC:40426 IMAGE:5178085, complete cds |
| NM_175907.3 | zinc binding alcohol dehydrogenase, domain containing 2 (ZADH2) |
| BC073782.1 | cDNA clone MGC:88796 IMAGE:6295732, complete cds |
| NM_004987.3 | LIM and senescent cell antigen-like-containing domain protein 1 |
| BC022362.1 | cDNA clone MGC:23888 IMAGE:4704496, complete cds |
| NM_004302 | Acti-Vin Rib Recombinant Human Protein |
| NM_003141.2 | tripartite motif-containing 21 (TRIM21) |
| NM_005522.3 | homeobox A1 (HOXA1), transcript variant 1 |
| NM_016011.2 | Trans-2-enoyl-CoA reductase, mitochondrial |
| NM_005734.1 | homeodomain interacting protein kinase 3 (HIPK3), transcript variant 1 |
| NM_004329 | BMPR1A Recombinant Human Protein |
| NP_002167.1 | Interferon beta/IFN-beta/IFNB Protein |
| BC014991.1 | N-methylpurine-DNA glycosylase (MPG) |
| NM_004527.2 | mesenchyme homeobox 1 (MEOX1), transcript variant 1 |
| BC014271.2 | endoglin (Osler-Rendu-Weber syndrome 1) (ENG) |
| XM_378660.1 | PREDICTED: *Homo sapiens* hypothetical LOC400584 (LOC400584) |
| NM_020467.2 | small trans-membrane and glycosylated protein (LOC57228), transcript variant 2 |
| BC033792.1 | tumor protein D52-like 3 (TPD52L3) |

TABLE 1-continued

Top 50 depleted markers.
Description of the top 50 depleted mixed-MS biomarkers.

| Database ID | Description |
| --- | --- |
| NM_007255.1 | xylosylprotein beta 1,4-galactosyltransferase, polypeptide 7 (galactosyltransferase 1) (B4GALT7) |
| BC017054.1 | methylenetetrahydrofolate dehydrogenase (NADP+ dependent) 2, methenyltetrahydrofolate cyclohydrolase (MTHFD2) |
| NM_180699.1 | small nuclear ribonucleoprotein 35kDa (U11/U12) (SNRNP35), transcript variant 3, mRNA. |
| NM_172159.2 | potassium voltage-gated channel, shaker-related subfamily, beta member 1 (KCNAB1), transcript variant 3 |
| NM_199183.1 | Putative testis serine protease 5 |
| BC002448.2 | actin binding LIM protein 1 (ABLIM1) |
| NM_005435.2 | Rho guanine nucleotide exchange factor (GEF) 5 (ARHGEF5) |
| BC006105.1 | chromosome 6 open reading frame 134 (C6orf134) |
| NM_005371.2 | methyltransferase like 1 (METTL1), transcript variant 1 |

TABLE 2

Top 50 RF only depleted markers.
Description of the top 50 RF only depleted MS biomarkers.

| Database ID | Description |
| --- | --- |
| NM_201998.1 | Splicing factor 1 |
| NM_020317.2 | chromosome 1 open reading frame 63 (C1orf63) |
| NM_016011.2 | Trans-2-enoyl-CoA reductase, mitochondrial |
| NM_004912.3 | KRIT1, ankyrin repeat containing (KRIT1), transcript variant 2 |
| BC028006.1 | inducible T-cell co-stimulator (ICOS) |
| NM_002642.1 | Phosphatidylinositol N-acetylglucosaminyltransferase subunit C |
| XM_379114.1 | hypothetical protein LOC150577 (LOC150577) |
| BC099907.1 | General transcription factor II-1 |
| NM_004987.3 | LIM and senescent cell antigen-like-containing domain protein 1 |
| BC089041.1 | Guanine nucleotide-binding protein subunit alpha-11 |
| NM_001008737.1 | hypothetical LOC401052 (LOC401052) |
| BC001419.1 | mitochondrial trans-2-enoyl-CoA reductase (MECR) |
| NM_003636.1 | potassium voltage-gated channel, shaker-related subfamily, beta member 2 (KCNAB2), transcript variant 1 |
| BC022258.1 | von Willebrand factor (VWF) |
| BC014271.2 | endoglin (Osler-Rendu-Weber syndrome 1) (ENG) |
| BC014991.1 | N-methylpurine-DNA glycosylase (MPG) |
| NM_180699.1 | small nuclear ribonucleoprotein 35 kDa (U11/U12) (SNRNP35), transcript variant 3, mRNA. |
| NMJ72159.2 | potassium voltage-gated channel, shaker-related subfamily, beta member 1 (KCNAB1), transcript variant 3 |
| BC022362.1 | cDNA clone MGC:23888 IMAGE:4704496, complete cds |
| BC003376.1 | ELAV (embryonic lethal, abnormal vision, *Drosophila*)-like 1 (Hu antigen R) (ELAVL1) |
| NM_018698.3 | nuclear transport factor 2-like export factor 2 (NXT2) |
| NM_005435.2 | Rho guanine nucleotide exchange factor (GEF) 5 (ARHGEF5) |
| BC002733.2 | chromosome 1 open reading frame 77 (C1orf77) |
| XM_086879.4 | PREDICTED: *Homo sapiens* hypothetical LOC150371 (LOC150371) |
| XM_003960444.1 | Hypothetical protein MGC21881 (MGC21881), mRNA |
| NM_031954.2 | potassium channel tetramerisation domain containing 10 (KCTD10) |
| NM_004302 | Acti-Vin R1b Recombinant Human Protein |
| BC002448.2 | actin binding LIM protein 1 (ABLIM1) |
| BC066948.1 | Ubiquitin-conjugating enzyme E2 S |
| PV4337 | LIM domain kinase 1 |
| BC029796.1 | hypothetical protein BC014011 (LOC116349) |
| XM_378514.1 | PREDICTED: *Homo sapiens* hypothetical protein LOC283663 (LOC283663), mRNA |
| NM_000148.2 | fucosyltransferase 1 (galactoside 2-alpha-L-fucosyltransferase, H blood group) (FUT1) |
| NM_175907.3 | zinc binding alcohol dehydrogenase, domain containing 2 (ZADH2) |
| NM_004527.2 | mesenchyme homeobox 1 (MEOX1), transcript variant 1 |
| BC033792.1 | tumor protein D52-like 3 (TPD52L3) |
| NM_003141.2 | tripartite motif-containing 21 (TRIM21) |
| BC029054.1 | PDZ domain containing 7 (PDZD7) |
| BC003065.1 | Cell division protein kinase 2 |
| NM_152716.1 | FLJ36874 protein (FLJ36874) |
| NM_002147.2 | homeobox B5 (HOXB5) |
| BC032451.1 | cDNA clone MGC:40426 IMAGE:5178085, complete cds |

TABLE 2-continued

Top 50 RF only depleted markers.
Description of the top 50 RF only depleted MS biomarkers.

| Database ID | Description |
| --- | --- |
| BC016380.1 | cDNA clone MGC:27376 IMAGE:4688477, complete cds |
| NM_005678.3 | SNRPN upstream reading frame (SNURF), transcript variant 1 |
| PV4202 | NIMA (never in mitosis gene a)-related kinase 1 (NEK1) |
| BC017054.1 | methylenetetrahydrofolate dehydrogenase (NADP+ dependent) 2, methenyltetrahydrofolate cyclohydrolase (MTHFD2) |
| NM_201403.1 | MOB1, Mps One Binder kinase activator-like 2C (yeast) (MOBKL2C), transcript variant 2 |
| NP_002167.1 | Interferon beta/IFN-beta/IFNB Protein |
| BC036884.1 | zinc finger protein 462 (ZNF462) |
| NM_005371.2 | methyltransferase like 1 (METTL1), transcript variant 1 |

TABLE 3

Top 50 expressed RRMS markers.
Description of the top 50 expressed RRMS biomarkers.

| Database ID | Description |
| --- | --- |
| NM_152729.2 | 5'-nucleotidase domain containing 1 (NT5DC1) |
| NM_005151.2 | ubiquitin specific peptidase 14 (tRNA-guanine transglycosylase) (USP14), transcript variant 1 |
| BC016380.1 | cDNA clone MGC:27376 IMAGE:4688477, complete cds |
| BC024289.1 | interferon, alpha-inducible protein 6 (IFI6) |
| BC032451.1 | cDNA clone MGC:40426 IMAGE:5178085, complete cds |
| NP_001954.2 | EGF/Epidermal Growth Factor Protein |
| NM_175907.3 | zinc binding alcohol dehydrogenase, domain containing 2 (ZADH2) |
| BC020233.1 | cDNA clone MGC:31936 IMAGE:4765518, complete cds |
| BC073782.1 | cDNA clone MGC:88796 IMAGE:6295732, complete cds |
| NP_001018016.1 | Mucin-1/MUC-1 Protein (Fc Tag) |
| NP_000868.1 | IL1R1/CD121a Protein |
| NM_004987.3 | LIM and senescent cell antigen-like-containing domain protein 1 |
| BC022362.1 | cDNA clone MGC:23888 IMAGE:4704496, complete cds |
| NM_004302 | Acti-Vin R1b Recombinant Human Protein |
| NP_061113.1 | TREM1 Protein |
| NM_003141.2 | tripartite motif-containing 21 (TRIM21) |
| BC030813.1 | cDNA clone MGC:22645 IMAGE:4700961, complete cds |
| BC030984.1 | cDNA clone MGC:32654 IMAGE:4701898, complete cds |
| NP_005009.2 | PD1/PDCD1 Protein |
| FGF2_Recombinant | FGF2 Recombinant Human Protein |
| NM_004329 | BMPR1A Recombinant Human Protein |
| NP_002167.1 | Interferon beta/IFN-beta/IFNB Protein |
| NM_182756.1 | speedy homolog A (Drosophila) (SPDYA), transcript variant 2 |
| NM_144606.1 | folliculin (FLCN), transcript variant 2 |
| BC014991.1 | N-methylpurine-DNA glycosylase (MPG) |
| NP_061947.1 | DLL4 Protein |
| PV3314 | Mitogen-activated protein kinase 1; see catalog number for detailed information on wild-type or point mutant status |
| NM_012289.2 | Kelch-like ECH-associated protein 1 |
| NP_003833.3 | TNFRSF10B/TRAILR2/CD262 Protein |
| BC014271.2 | endoglin (Osler-Rendu-Weber syndrome 1) (ENG) |
| NM_013246.1 | cardiotrophin-like cytokine factor 1 (CLCF1) |
| BC064612.1 | myeloid/lymphoid or mixed-lineage leukemia (trithorax homolog, Drosophila); translocated to, 6 (MLLT6) |
| NP_001233.1 | CD27/TNFRSF7 Protein |
| NM_003798.1 | Alpha-catulin |
| NM_145253.1 | LOC124402 (LOC124402), mRNA |
| NM_172238.1 | Transcription factor AP-2 delta (activating enhancer binding protein 2 delta) (TFAP2D), mRNA |
| P01566 | Interferon alpha 10/IFNA10 Protein |
| BC026101.2 | nudE nuclear distribution gene E homolog (A. nidulans)-like 1 (NDEL1) |
| NP_004084.1 | EphrinB2/EFNB2 Protein |
| NM_012325.1 | microtubule-associated protein, RP/EB family, member 1 (MAPRE1) |
| NP_001019799.1 | NRP1/Neuropilin-1 Protein |
| NM_020317.2 | chromosome 1 open reading frame 63 (C1orf63) |
| NM_014481.2 | APEX nuclease (apurinic/apyrimidinic endonuclease) 2 (APEX2), nuclear gene encoding mitochondrial protein |
| NM_172160.1 | potassium voltage-gated channel, shaker-related subfamily, beta member 1 (KCNAB1), transcript variant 1 |
| BC011600.1 | cDNA clone IMAGE:3050953, **** WARNING: chimeric clone **** |

TABLE 3-continued

Top 50 expressed RRMS markers.
Description of the top 50 expressed RRMS biomarkers.

| Database ID | Description |
| --- | --- |
| NP_068576.1 | ACE2/ACEH Protein |
| BC032347.1 | chromosome 8 open reading frame 59 (C8orf59) |
| NM_201433.1 | Growth arrest-specific 7 (GAS7), transcript variant c, mRNA |
| NM_004078.1 | cysteine and glycine-rich protein 1 (CSRP1) |
| BC028006.1 | inducible T-cell co-stimulator (ICOS) |

TABLE 4

Top 50 expressed SPMS markers.
Description of the top 50 expressed SPMS biomarkers.

| Database ID | Description |
| --- | --- |
| NP_002497.2 | B-NGF/Beta-NGF Protein (Native) |
| NP_001001547.1 | CD36/SCARB3 Protein (His Tag) |
| NM_004493.1 | hydroxysteroid (17-beta) dehydrogenase 10 (HSD17B10), nuclear gene encoding mitochondrial protein, transcript variant 1 |
| NM_018464.2 | CDGSH iron sulfur domain 1 (CISD1) |
| BC010467.1 | cDNA clone MGC:17410 IMAGE:4156035, complete cds |
| NM_002399.2 | Meis homeobox 2 (MEIS2), transcript variant f |
| BC066340.1 | Biogenesis of lysosome-related organelles complex 1 subunit 1 |
| NM_004596.1 | small nuclear ribonucleoprotein polypeptide A (SNRPA) |
| NM_016401.2 | chromosome 11 open reading frame 73 (C11orf73) |
| NM_005409.3 | C-X-C motif chemokine 11 |
| BC026039.1 | mitochondrial GTPase 1 homolog (*S. cerevisiae*) (MTG1) |
| NM_003887.1 | Development and differentiation-enhancing factor 2 |
| BC009873.1 | cDNA clone IMAGE:3946787, partial cds |
| NM_138819.1 | family with sequence similarity 122C (FAM122C) |
| NM_005307.1 | G protein-coupled receptor kinase 4 |
| NM_144647.1 | Calcyphosin-like protein |
| NM_004202.1 | Thymosin beta-4, Y-chromosomal |
| NM_182772.1 | CAMP responsive element modulator (CREM), transcript variant 16, mRNA |
| NM_001130.5 | Amino-terminal enhancer of split |
| BC016789.1 | glycine-N-acyltransferase-like 2 (GLYATL2) |
| IGFBP6_Recombinant | IGFBP6 Recombinant Human Protein |
| BC048299.1 | spermatogenesis associated, serine-rich 2 (SPATS2) |
| BC104469.1 | Outer dense fiber protein 3-like protein 2 |
| NM_007006.1 | nudix (nucleoside diphosphate linked moiety X)-type motif 21 (NUDT21) |
| NM_022788.2 | purinergic receptor P2Y, G-protein coupled, 12 (P2RY12), transcript variant 1 |
| NP_000556.1 | IL6R/CD126 Protein (His Tag) |
| NM_181270.1 | CKLF-like MARVEL transmembrane domain-containing protein 1 |
| NM_201403.1 | MOB1, Mps One Binder kinase activator-like 2C (yeast) (MOBKL2C), transcript variant 2 |
| NM_015399.1 | breast cancer metastasis suppressor 1 (BRMS1), transcript variant 1 |
| XM_379668.2 | PREDICTED: *Homo sapiens* hypothetical protein LOC286208 (LOC286208), mRNA. |
| BC042428.1 | collagen, type XXIII, alpha 1 (COL23A1) |
| BC017440.1 | trafficking protein particle complex 2-like (TRAPPC2L) |
| NM_81349.1 | SMAD specific E3 ubiquitin protein ligase 1 (SMURF 1), transcript variant 2 |
| BC035143.1 | Tigger transposable element-derived protein 1 |
| BC007412.1 | chromosome 14 open reading frame 153 (C14orf153) |
| NMJ39280.1 | ORM1-like 3 (*S. cerevisiae*) (ORMDL3) |
| NM_181640.1 | Chemokine-like factor (CKLF), transcript variant 2, mRNA |
| BC009650.1 | PDS5, regulator of cohesion maintenance, homolog A (*S. cerevisiae*) (SCC-112) |
| NM_025187.2 | chromosome 16 open reading frame 70 (C16orf70) |
| NM_003512.3 | Histone H2A type 1-C |
| NM_015698.2 | G patch domain and KOW motifs (GPKOW) |
| BC017180.2 | Staphylococcal nuclease domain-containing protein 1 |
| NM_001136.2 | advanced glycosylation end product-specific receptor (AGER), transcript variant 1 |
| NM_207013.1 | transcription elongation factor B (SIII), polypeptide 2 (18 kDa, elongin B) (TCEB2), transcript variant 2 |
| BC007340.1 | Bystin |
| BC093661.1 | Putative uncharacterized protein C14orf177 |
| NM_031473.1 | Intraflagellar transport protein 81 homolog |
| BC033195.1 | killer cell immunoglobulin-like receptor, three domains, X1 (KIR3DX1) |

TABLE 4-continued

Top 50 expressed SPMS markers.
Description of the top 50 expressed SPMS biomarkers.

| Database ID | Description |
|---|---|
| BC014475.1 | baculoviral IAP repeat-containing 7 (livin) (BIRC7) |
| NM_133640.3 | Mediator of RNA polymerase II transcription subunit 22 |

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction and/or assay conditions with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials

Unless described otherwise, the materials used in the experiments were obtained from commercial sources or obtained by methods known in the art, and used without further purification.

Study Population

Thirty-one relapsing-remitting multiple sclerosis (RRMS) and twenty secondary progressive multiple sclerosis (SPMS) serum samples were obtained from BioServe Biotechnologies, Ltd. (Beltsville, MD). Fifteen early-stage PD samples were obtained from the Parkinson's Study Group (Boston, MA), and fifteen stage 3-4 breast cancer samples were obtained from BioServe Biotechnologies, Ltd. Healthy control samples were obtained from a variety of sources, including two from Analytical Biological Systems, Inc. (Wilmington, DE), twenty-eight from BioServe Biotechnologies, Ltd., and one from Asterand, Inc (Detroit, MI). All samples were handled using standard procedures and stored at −80° C. until use, and freezer conditions were monitored using Sensaphone 1400 (Phonetics, Inc., Aston, PA). Demographic characteristics of the study population are listed in the Table found in FIG. 3.

Human Protein Microarrays

To identify autoantibodies in human sera, Invitrogen's ProtoArray v5.1 Human Protein Microarrays were used (Cat. No. PAH0525020, Invitrogen, Carlsbad, CA, USA), each containing 9,486 unique human protein antigens. All proteins were expressed as GST fusion proteins in insect cells, purified under native conditions, and spotted in duplicate onto nitrocellulose-coated glass slides. Arrays were probed with serum and scanned according to the manufacturer's instructions using commercially prepared reagents. Microarray slides were blocked (Blocking Buffer, Cat. No. PA055, Invitrogen) and then each was incubated with serum diluted to 1:500 in washing buffer. After washing, arrays were probed with anti-human IgG (H+L) conjugated to AlexaFluor 647 (Cat. No. A-21445, Invitrogen). Arrays were then washed, dried, and immediately scanned with a GenePix 4000B Fluorescence Scanner (Molecular Devices, Sunnyvale, CA, USA).

Microarray Data Analysis

Fluorescence data were acquired by aligning the Genepix Array List onto the microarray image using the Genepix Pro analysis software. The resulting Genepix results files were imported into Invitrogen's PROSPECTOR® 5.2 for analysis. The "group characterization" and "two-group comparison" features in the Immune Response Biomarker Profiling (IRBP) toolbox within PROSPECTOR® then enabled M-statistical analysis of the differential autoantibody expression between the two groups being compared. Positive hits were determined by a Z-Factor >0.4 and a minimum signal intensity of 1500 RFU, which allow for stringent biomarker selection and minimize the number of false positives. Autoantibodies were sorted into descending order by difference of prevalence between MS and control groups, and the top 50 most differentially expressed autoantibodies in the MS group were chosen as potential MS diagnostic biomarkers and tested further. Additionally, a second round of biomarker selection was carried out by sorting autoantibodies in descending order by difference of prevalence between control and MS groups. This time, the 50 most differentially expressed autoantibodies in the control group, putatively reflecting the selective depletion of these blood-borne autoantibodies in the MS group, were also chosen as potential diagnostic biomarkers and tested. All data are MIAME compliant and raw data from the microarrays have been deposited in a MIAME compliant database (GEO) under accession number (GSE95718).

Subjects were randomly split into Testing and Training Sets, such that both sets included cases and controls matched by age and gender. The Training Set was used to rank candidate protein biomarkers by their predictive power and to establish the diagnostic logic. The initial Training Set for the MS group consisted of 26 MS and 16 control samples; the remaining samples were relegated to the independent Testing Set, containing 25 MS and 15 control subjects. The predictive classification accuracy of the selected biomarkers in the Training Set, Testing Set, and in both sets combined was tested with *R's Random Forest* (RF; v 4.6-10), using the default settings (Breiman, Random Forests. *Machine Learning*. 2001; 45:5-32). Selected biomarkers were tested with the RF model algorithm, and classification accuracy is reported in a confusion matrix and misclassifications as an out-of-bag (OOB) error score. Receiver Operating Characteristic (ROC) curves, widely used to evaluate the utility of diagnostic tests, were generated using R (3.02) packages ROCR (v 1.0-5) and pROC (v 1.7.3). Based on the determined optimal number of autoantibody biomarker panel members, a final model was constructed using these biomarkers and their associated Training Set logic and further tested with the independent Testing Set subject samples.

Using the same Training and Testing Set strategy outlined above, an additional round of biomarker discovery was performed using only RF, instead of prevalence difference, to select potential biomarkers. After M-statistical analysis by Prospector, the data were analyzed using the "variable importance" function in RF, which is the prediction accuracy of the OOB error score reported for each decision tree, and also for each individual permutated biomarker. The difference between the two values was averaged over all trees and normalized by the standard error. The 50 most differentially depleted biomarkers in the MS group compared to controls based on the normalized variable importance score were chosen as potential diagnostic biomarkers and further analyzed for their diagnostic value as reported above.

Selected results of the present invention are illustrated herein.

Example 1. Selection of a Panel of Autoantibody Biomarkers for Diagnosis of MS A panel of autoantibodies capable of detecting the presence of MS pathology in a mixed-subtype population of MS patient samples was identified as follows. Serum samples from 51 MS patients with a clinical diagnosis of either Relapsing-Remitting MS (RRMS) or Secondary-Progressive MS (SPMS), the two most prevalent MS subtypes, and thirty-one age- and gender-matched control samples were randomly separated into either a Training Set (16 RRMS, 10 SPMS and 16 controls) or Testing Set (15 RRMS, 10 SPMS and 15 controls), each containing roughly equal proportions of both MS subtypes. Training and Testing Set sera were used to probe commercially available human protein microarrays containing 9,486 protein targets. Autoantibody profiles from the MS and control subjects in the Training Set were compared using PROSPECTOR® microarray analysis software, which identified 54 autoantibodies with a significantly (P<0.05) higher prevalence in the MS group compared to the control group in the Training Set as potential diagnostic biomarkers. From this list, the top 50 most differentially expressed autoantibodies in the MS group were chosen as a working diagnostic biomarker panel.

Example 2. Verification of Differentially Expressed MS Biomarkers Via Training and Testing Set Analysis The 50 most differentially expressed autoantibody biomarkers chosen from the MS Training Set were evaluated for their prediction accuracy using Random Forest (RF). Using the 50 selected biomarkers in RF, MS subjects were distinguished from age- and gender-matched control subjects in the Training Set (n=42; 26 MS, 16 controls) with an average 72.4% prediction accuracy based on five replicate runs. The classification potential of the 50 biomarkers was evaluated using the RF Training Set logic to classify MS in the Testing Set subjects, an independent group of samples that played no role in biomarker selection. RF correctly classified an average of 82.5% of MS and controls among Testing Set subjects (n=40; 25 MS, 15 controls), again based on an average of five replicate runs.

Example 3. Selection and Verification of Useful MS Biomarkers that are Selectively Depleted from the Sample Biomarker selection described above was based on the increased production and expression of autoantibody biomarkers in the blood. Although not wishing to be bound by any particular theory, it is presumed that these biomarkers are expressed in response to MS-associated cell and tissue debris production. Since MS is well-known to have an autoimmune component, the possibility was examined that disease onset and progression could instead be linked to a selective depletion of autoantibodies that are normally present in the blood.

To examine this, the autoantibody profile expression data generated by PROSPECTOR® from the Training Set samples described elsewhere herein was examined. A total of 3,076 autoantibodies with a significantly (P<0.05) lower prevalence in the MS group compared to the control group were identified. From this list, the 50 most differentially depleted autoantibodies in the MS group were chosen as the new working diagnostic biomarker panel. The new panel of depleted MS autoantibody biomarkers chosen from the Training Set were re-verified as significant predictors using RF. MS subjects in the Training Set (n=42; 26 MS, 16 controls) were distinguished from controls with an average 95.8% prediction accuracy. Furthermore, RF correctly classified 95.0% of MS and controls among Testing Set subjects (n=40; 25 MS, 15 controls). Finally, combining both Training and Testing Set samples and using the Training Set logic, RF successfully distinguished MS from controls with an overall accuracy of 96.8%. All Training and Testing Set comparisons mentioned above are based on results from an average of five replicate runs. ROC curve analysis of the overall utility of the depleted MS biomarkers for detection of MS in the Testing Set subjects revealed an area under the curve (AUC) of 0.94, indicating excellent classification accuracy (FIG. 1).

Diagnostic sensitivity, specificity, and positive- and negative-predictive values (PPV and NPV) for the 50 depleted MS biomarkers used to evaluate the Testing Set subjects are shown in the Tables found in FIGS. 4-5. Subsequent tests and comparisons carried out in the present disclosure and described elsewhere herein refer to the use of the depleted autoantibody biomarker panel described here and shown in Table 1, unless otherwise noted.

Example 4. Exchanging Training and Testing Sets Yields Similar Biomarker Panels with Comparable Diagnostic Accuracy To further demonstrate and confirm the utility of depleted autoantibodies as biomarkers for the detection of MS pathology in a separate set of patient samples, a second round of MS biomarker discovery was carried out as follows. The subjects used in the Training and Testing Sets were exchanged, and the identities and diagnostic performance of the second round of depleted MS biomarkers were compared with those chosen in the first round. There was a 60% overlap between the second round biomarkers and those chosen in the first round. Using this new panel of 50 second round biomarkers, RF was able to correctly classify over 99.0% of MS and controls in Testing Set subjects (sensitivity=100.0%; specificity=93.8%; PPV=96.3%; NPV=100.0%; ROC AUC=1).

Example 5. Validation of the MS Biomarker Panel Using Two Biomarker Selection Strategies: RF Vs. Prevalence Difference An additional and unbiased MS biomarker selection process using RF only was also carried out. As described in the methods section, RF was used to independently choose potential MS biomarkers instead of ranking biomarkers based on prevalence difference through PROSPECTOR®. Using the panel of 50 RF-selected biomarkers, RF was able to correctly classify MS and controls in Testing Set subjects with an average of 92.5% overall accuracy in five replicate runs, thus with comparable accuracy to both panels derived from prevalence difference described above. 38 of 50 (76%) of the RF-selected biomarkers overlapped with the differentially depleted biomarkers described in Example 3.

Example 6. Fewer than 50 Autoantibody Biomarkers are Sufficient for Accurate Detection of MS To determine the minimum number of autoantibody biomarkers required to achieve the best diagnostic accuracy, the 50 depleted MS biomarkers were first sorted according to decreasing relative importance, and then successively removed from the bottom of the list until the overall diagnostic accuracy began to decline significantly. Using this approach, it was determined that a panel of three biomarkers (the top three biomarkers listed in Table 1) was the minimum number required to maintain an effective diagnostic accuracy in Testing Set subjects, demonstrating an overall accuracy of 92.5% (sensitivity=96.0%; specificity=86.7%; ROC AUC=0.95) for distinguishing MS subjects from age- and gender-matched controls (FIG. 1; Tables found in FIGS. 4-5).

Example 7. Disease Specificity of the Selected Depleted Biomarkers for MS

The disease specificity of the selected panel of depleted biomarkers described above in Section 3.3 for the detection of MS was evaluated, with the goal of determining whether these biomarkers can successfully differentiate MS subjects from those with other neurological and non-neurological diseases. To eliminate the possibility that the selected biomarkers were simply detecting nonspecific disease, the same 25 MS sera from Testing Set subjects were compared to sera obtained from 15 subjects with stage 3-4 breast cancer and 15 subjects with early-stage Parkinson's Disease (PD). Using the original panel of 50 biomarkers, MS sera were readily distinguished from breast cancer sera with an overall accuracy of 100.0% (sensitivity=100.0%; specificity=100.0%; ROC AUC=1) (Tables found in FIGS. 4 and 5). By contrast, MS subjects could not be accurately distinguished from early-stage PD subjects, with results showing 40.0% overall accuracy (sensitivity=48.0%; specificity=26.7%; ROC AUC=0.72). The inability to distinguish MS from early-stage PD could indicate a potential overlap in disease pathology and therefore autoantibody biomarkers, which could complicate this distinction.

Example 8. Subtyping of MS: Discrete Autoantibody Biomarker Panels can Distinguish Relapsing-Remitting MS from Secondary Progressive MS The use of autoantibody biomarkers to distinguish between different subtypes of MS was evaluated as follows. While the majority of MS patients are initially diagnosed as RRMS, a significant fraction of these patients will eventually progress to SPMS for unknown reasons. To address this aspect of MS disease progression, two additional rounds of biomarker discovery were performed to generate panels of subtype-specific expression biomarkers.

Figure 2:
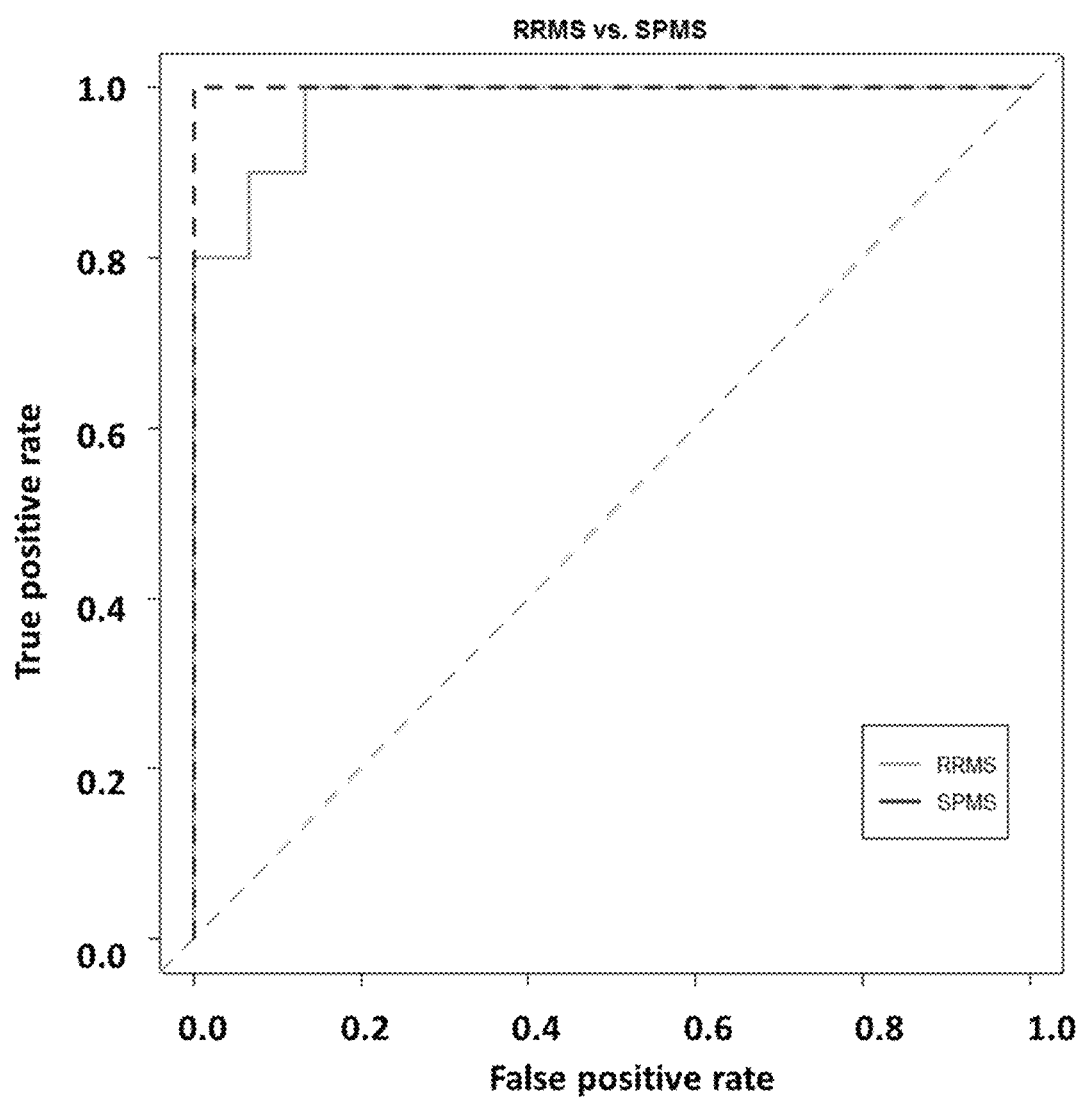
FIG. 2 is a graph illustrating biomarker analysis and Receiver Operating Characteristic (ROC) curve assessment of diagnostic utility of autoantibody biomarkers for subtyping and pathological progression of MS. Comparison of Testing Set relapsing-remitting MS (RRMS) subjects (n=15) vs. Testing Set secondary progressive MS subjects (n=10) using a panel of 50 RRMS (dashed line) or SPMS (solid line) specific biomarkers demonstrates that these biomarkers can be used to accurately distinguish between these two different stages of MS progression.

RRMS (n=31) and SPMS (n=20) samples were separated into a Training (n=26; 16 RRMS, 10 SPMS) and Testing Set (n=25; 15 RRMS, 10 SPMS), using the same strategy as described above. The top 50 most differentially expressed autoantibody biomarkers in each MS subtype compared to the other were selected and verified as significant using the methods described above; see Tables 3-4. Using RRMS-specific biomarkers and the RF logic derived from the Training Set, RRMS sera were readily distinguished from SPMS sera with an overall accuracy of 100% in both Training and Testing Set comparisons. Similarly, using SPMS-specific biomarkers and RF logic derived from the Training Set, SPMS sera were readily distinguished from RRMS sera with an overall accuracy of 96.2% in the Training Set, and 92.0% in the Testing Set. Results from ROC curve analyses of these comparisons are presented in FIG. 2. These results confirm that, although RRMS and SPMS are different stages of the same disease and are expected to share biomarkers, the panels of subtype-specific autoantibody biomarkers selected here along with their corresponding diagnostic logic were capable of differentiating the pathology of different stages of MS progression.

The disclosures of each and every patent, patent application, and publication cited herein are hereby incorporated herein by reference in their entirety.

While the invention has been disclosed with reference to specific embodiments, it is apparent that other embodiments and variations of this invention can be devised by others skilled in the art without departing from the true spirit and scope of the invention. The appended claims are intended to be construed to include all such embodiments and equivalent variations.

What is claimed is:

1. A method for detecting multiple sclerosis (MS) diagnostic autoantibodies in a subject, the method comprising:
    (a) contacting an immunoglobulin-containing biological sample from the subject with a system comprising antigens that form immunocomplexes with MS diagnostic autoantibodies, said antigens comprising general transcription factor II-I, splicing factor 1, and inducible T-cell co-stimulator (ICOS), to form a reaction mixture, under conditions that allow for formation in the reaction mixture of an immunocomplex between each antigen and its corresponding MS diagnostic autoantibody, if its corresponding MS diagnostic autoantibody is present in the sample; and
    (b) detecting presence or absence of immunocomplexes in the reaction mixture, wherein formation of immunocomplexes between the antigens and their corresponding MS diagnostic autoantibodies indicates presence of the MS diagnostic autoantibodies in the biological sample.

2. The method of claim 1, wherein the system further comprises at least one antigen selected from the group consisting of chromosome 1 open reading frame 63 (C1orf63); hypothetical LOC401052 (LOC401052); KRIT1, ankyrin repeat containing (KRIT1), transcript variant 2; mitochondrial trans-2-enoyl-CoA reductase (MECR); phosphatidylinositol N-acetylglucosaminyltransferase subunit C; and trans-2-enoyl-CoA reductase, mitochondrial.

3. The method of claim 1, wherein the system further comprises antigens mitochondrial trans-2-enoyl-CoA reductase (MECR); and trans-2-enoyl-CoA reductase, mitochondrial.

4. The method of claim 1, wherein the subject is a human.

5. The method of claim 1, wherein the biological sample is selected from the group consisting of whole blood, plasma, serum, cerebrospinal fluid, saliva, and sputum.

6. The method of claim 1, wherein each one of the antigens is attached to a solid substrate.

7. The method of claim 6, wherein the solid substrate comprises beads or a microfluidic biosensor, or the solid substrate is in the form of an array.

8. The method of claim 7, wherein the array is a microarray and comprises a nitrocellulose-coated glass slide.

9. The method of claim 1, wherein the immunocomplexes are detected using an immunoassay selected from the group consisting of competition assay, direct immunoassay, indirect immunoassay, immunoprecipitation, immunoblotting, and sandwich immunoassay.

10. The method of claim 1, further comprising at least one of advising the subject to be administered a therapeutic agent, advising the subject to receive therapeutic intervention for MS, and administering to the subject a therapeutic agent or a therapeutic intervention to treat MS.

11. A method of generating a subject-specific, MS diagnostic autoantibody profile for a subject, the method comprising:
(a) contacting an immunoglobulin-containing biological sample from the subject with a system comprising antigens that form immunocomplexes with MS diagnostic autoantibodies, said antigens comprising general transcription factor II-I, splicing factor 1, and inducible T-cell co-stimulator (ICOS), to form a reaction mixture, under conditions that allow for formation in the reaction mixture of an immunocomplex between each antigen and its corresponding MS diagnostic autoantibody, if its corresponding MS diagnostic autoantibody is present in the sample;
(b) detecting presence or absence of immunocomplexes in the reaction mixture, wherein formation of immunocomplexes between the antigens and their corresponding MS diagnostic autoantibodies indicates presence of the MS diagnostic autoantibodies in the biological sample; and
(c) generating a subject-specific MS diagnostic autoantibody profile of MS diagnostic autoantibodies present in the biological sample.

12. The method of claim 11, wherein the system further comprises at least one antigen selected from the group consisting of chromosome 1 open reading frame 63 (C1orf63); hypothetical LOC401052 (LOC401052); KRIT1, ankyrin repeat containing (KRIT1), transcript variant 2; mitochondrial trans-2-enoyl-CoA reductase (MECR); phosphatidylinositol N-acetylglucosaminyltransferase subunit C; and trans-2-enoyl-CoA reductase, mitochondrial.

13. The method of claim 11, wherein the system further comprises antigens mitochondrial trans-2-enoyl-CoA reductase (MECR); and trans-2-enoyl-CoA reductase, mitochondrial.

14. The method of claim 11, wherein the subject is a human.

15. The method of claim 11, wherein the biological sample is selected from the group consisting of whole blood, plasma, serum, cerebrospinal fluid, saliva, and sputum.

16. The method of claim 11, wherein each one of the antigens is attached to a solid substrate.

17. The method of claim 16, wherein the solid substrate comprises beads or a microfluidic biosensor, or the solid substrate is in the form of an array.

18. The method of claim 17, wherein the array is a microarray and comprises a nitrocellulose-coated glass slide.

19. The method of claim 11, wherein the immunocomplexes are detected using an immunoassay selected from the group consisting of competition assay, direct immunoassay, indirect immunoassay, immunoprecipitation, immunoblotting, and sandwich immunoassay.

20. The method of claim 11, further comprising at least one of advising the subject to be administered a therapeutic agent, advising the subject to receive therapeutic intervention for MS, and administering to the subject a therapeutic agent or a therapeutic intervention to treat MS.

* * * * *